US009839472B2

(12) United States Patent
Rioux et al.

(10) Patent No.: US 9,839,472 B2
(45) Date of Patent: *Dec. 12, 2017

(54) SCREEN SPHERE TISSUE ABLATION DEVICES AND METHODS

(71) Applicant: Innoblative Designs, Inc., Chicago, IL (US)

(72) Inventors: Robert F. Rioux, Ashland, MA (US); Ryan M. Bean, Westminster, MA (US)

(73) Assignee: Innoblative Designs, Inc., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/624,327

(22) Filed: Jun. 15, 2017

(65) Prior Publication Data

US 2017/0281267 A1   Oct. 5, 2017

Related U.S. Application Data

(63) Continuation of application No. 15/337,334, filed on Oct. 28, 2016.
(Continued)

(51) Int. Cl.
*A61B 18/14* (2006.01)
*A61B 18/12* (2006.01)
*A61B 18/00* (2006.01)

(52) U.S. Cl.
CPC ...... *A61B 18/1482* (2013.01); *A61B 18/1206* (2013.01); *A61B 2018/0022* (2013.01);
(Continued)

(58) Field of Classification Search
CPC ............... A62B 18/1206; A62B 18/14; A62B 2218/002; A61B 2018/0022;
(Continued)

(56) References Cited

U.S. PATENT DOCUMENTS 4,699,147 A   10/1987   Chilson et al.
4,976,711 A   12/1990   Parins et al.
(Continued)

FOREIGN PATENT DOCUMENTS

CN   2610858 Y   4/2004
DE   102010032932 A1   2/2012
(Continued)

OTHER PUBLICATIONS

"Aquamantys System" Product Brochure, Medtronic, 2014 (12 Pages).
(Continued)

*Primary Examiner* — Michael Peffley
(74) *Attorney, Agent, or Firm* — Brown Rudnick LLP

(57) ABSTRACT

The present invention is an ablation device having a screen sphere configuration for the ablation of marginal tissue surrounding a tissue cavity. The device includes a probe having a nonconductive elongated shaft including at least one lumen therethrough and a nonconductive distal portion extending from the shaft. The nonconductive distal portion includes a plurality distal ports and a plurality of proximal ports in communication with the at least one lumen of the shaft. The device further includes an electrode array including a plurality of independent conductive wires extending through the lumen and positioned along an external surface of the nonconductive distal portion, each of the plurality of wires passes through at least an associated one of the proximal ports and through at least a corresponding one of the distal ports.

12 Claims, 24 Drawing Sheets

Related U.S. Application Data

(60) Provisional application No. 62/275,984, filed on Jan. 7, 2016, provisional application No. 62/248,157, filed on Oct. 29, 2015.

(52) U.S. Cl.
CPC ............ *A61B 2018/00333* (2013.01); *A61B 2018/00577* (2013.01); *A61B 2018/1467* (2013.01); *A61B 2218/002* (2013.01)

(58) Field of Classification Search
CPC ........... A61B 2018/00238; A61B 2018/00333; A61B 2018/00577; A61B 2018/1467
See application file for complete search history.

(56) References Cited

U.S. PATENT DOCUMENTS

| | | |
|---|---|---|
| 4,979,948 A | 12/1990 | Geddes et al. |
| 5,045,056 A | 9/1991 | Behl |
| 5,100,423 A | 3/1992 | Fearnot |
| 5,117,828 A | 6/1992 | Metzger et al. |
| 5,334,193 A | 8/1994 | Nardella |
| 5,429,605 A | 7/1995 | Richling et al. |
| 5,471,982 A | 12/1995 | Edwards et al. |
| 5,472,441 A | 12/1995 | Edwards et al. |
| 5,486,161 A | 1/1996 | Lax et al. |
| 5,536,267 A | 7/1996 | Edwards et al. |
| 5,562,720 A | 10/1996 | Stern et al. |
| 5,657,760 A | 8/1997 | Ying et al. |
| 5,672,153 A | 9/1997 | Lax et al. |
| 5,672,173 A | 9/1997 | Gough et al. |
| 5,672,174 A | 9/1997 | Gough et al. |
| 5,683,384 A | 11/1997 | Gough et al. |
| 5,713,942 A | 2/1998 | Stern et al. |
| 5,728,143 A | 3/1998 | Gough et al. |
| 5,772,590 A | 6/1998 | Webster, Jr. |
| 5,782,827 A | 7/1998 | Gough et al. |
| 5,827,276 A | 10/1998 | LeVeen et al. |
| 5,840,076 A | 11/1998 | Swanson et al. |
| 5,846,239 A | 12/1998 | Swanson et al. |
| 5,855,576 A | 1/1999 | LeVeen et al. |
| 5,863,290 A | 1/1999 | Gough et al. |
| 5,868,736 A | 2/1999 | Swanson et al. |
| 5,868,776 A | 2/1999 | Wright |
| 5,871,483 A | 2/1999 | Jackson et al. |
| 5,888,198 A | 3/1999 | Eggers et al. |
| 5,891,136 A | 4/1999 | McGee et al. |
| 5,893,847 A * | 4/1999 | Kordis ................ A61B 5/0422 600/374 |
| 5,913,855 A | 6/1999 | Gough et al. |
| 5,928,229 A | 7/1999 | Gough et al. |
| 5,935,123 A | 8/1999 | Edwards et al. |
| 5,961,513 A | 10/1999 | Swanson et al. |
| 5,980,517 A | 11/1999 | Gough |
| 6,009,877 A | 1/2000 | Edwards |
| 6,032,077 A | 2/2000 | Pomeranz |
| 6,036,689 A | 3/2000 | Tu et al. |
| 6,053,913 A | 4/2000 | Tu et al. |
| 6,053,937 A | 4/2000 | Edwards et al. |
| 6,063,081 A | 5/2000 | Mulier et al. |
| 6,071,278 A | 6/2000 | Panescu et al. |
| 6,071,280 A | 6/2000 | Edwards et al. |
| 6,099,526 A | 8/2000 | Whayne et al. |
| 6,112,123 A | 8/2000 | Kelleher et al. |
| 6,123,718 A | 9/2000 | Tu et al. |
| 6,142,993 A | 11/2000 | Whayne et al. |
| 6,221,071 B1 | 4/2001 | Sherry et al. |
| 6,241,666 B1 | 6/2001 | Pomeranz et al. |
| 6,251,109 B1 | 6/2001 | Hassett et al. |
| 6,258,087 B1 | 7/2001 | Edwards et al. |
| 6,309,352 B1 | 10/2001 | Oraevsky et al. |
| 6,312,408 B1 | 11/2001 | Eggers et al. |
| 6,312,429 B1 | 11/2001 | Burbank et al. |
| 6,358,248 B1 | 3/2002 | Mulier et al. |
| 6,379,353 B1 | 4/2002 | Nichols |
| 6,409,722 B1 | 6/2002 | Hoey et al. |
| 6,425,877 B1 | 7/2002 | Edwards |
| 6,454,766 B1 | 9/2002 | Swanson et al. |
| 6,491,710 B2 | 12/2002 | Satake |
| 6,494,902 B2 | 12/2002 | Hoey et al. |
| 6,503,247 B2 | 1/2003 | Swartz et al. |
| 6,522,930 B1 | 2/2003 | Schaer et al. |
| 6,537,248 B2 | 3/2003 | Mulier et al. |
| 6,537,272 B2 | 3/2003 | Christopherson et al. |
| 6,544,262 B2 | 4/2003 | Fleischman |
| 6,551,310 B1 | 4/2003 | Ganz et al. |
| 6,585,732 B2 | 7/2003 | Mulier et al. |
| 6,623,481 B1 | 9/2003 | Garbagnati et al. |
| 6,638,275 B1 | 10/2003 | McGaffigan et al. |
| 6,648,883 B2 | 11/2003 | Francischelli et al. |
| 6,692,466 B1 | 2/2004 | Chow et al. |
| 6,736,810 B2 | 5/2004 | Hoey et al. |
| 6,736,811 B2 | 5/2004 | Panescu et al. |
| 6,743,226 B2 | 6/2004 | Cosman et al. |
| 6,764,487 B2 | 7/2004 | Mulier et al. |
| 6,780,183 B2 | 8/2004 | Jimenez, Jr. et al. |
| 6,805,131 B2 | 10/2004 | Kordis |
| 6,826,421 B1 | 11/2004 | Beatty et al. |
| 6,849,073 B2 | 2/2005 | Hoey et al. |
| 6,872,206 B2 | 3/2005 | Edwards et al. |
| 6,878,149 B2 | 4/2005 | Gatto |
| 6,955,641 B2 | 10/2005 | Lubock |
| 6,978,788 B2 | 12/2005 | Klimberg et al. |
| 6,984,232 B2 | 1/2006 | Vanney et al. |
| 7,104,989 B2 | 9/2006 | Skarda |
| 7,150,745 B2 | 12/2006 | Stern et al. |
| 7,156,845 B2 | 1/2007 | Mulier et al. |
| 7,169,144 B2 | 1/2007 | Hoey et al. |
| 7,247,155 B2 | 7/2007 | Hoey et al. |
| 7,276,061 B2 | 10/2007 | Schaer et al. |
| 7,306,593 B2 | 12/2007 | Keidar et al. |
| 7,326,208 B2 | 2/2008 | Vanney et al. |
| 7,344,535 B2 | 3/2008 | Stern et al. |
| 7,364,579 B2 | 4/2008 | Mulier et al. |
| 7,367,972 B2 | 5/2008 | Francischelli et al. |
| 7,371,231 B2 | 5/2008 | Rioux et al. |
| 7,399,299 B2 | 7/2008 | Daniel et al. |
| 7,416,552 B2 | 8/2008 | Paul et al. |
| 7,419,489 B2 | 9/2008 | Vanney et al. |
| 7,556,628 B2 | 7/2009 | Utley et al. |
| 7,632,268 B2 | 12/2009 | Edwards et al. |
| 7,717,909 B2 | 5/2010 | Strul et al. |
| 7,769,432 B2 | 8/2010 | Klimberg et al. |
| 7,776,034 B2 | 8/2010 | Kampa |
| 7,828,793 B2 | 11/2010 | Thompson et al. |
| 7,862,498 B2 | 1/2011 | Nguyen et al. |
| 7,879,030 B2 | 2/2011 | Paul et al. |
| 7,942,873 B2 | 5/2011 | Kwan et al. |
| 7,959,628 B2 | 6/2011 | Schaer et al. |
| 7,959,631 B2 | 6/2011 | DiCarlo |
| 8,034,022 B2 | 10/2011 | Boatman |
| 8,043,289 B2 | 10/2011 | Behl et al. |
| 8,048,069 B2 | 11/2011 | Skwarek et al. |
| 8,114,071 B2 | 2/2012 | Woloszko et al. |
| 8,224,416 B2 * | 7/2012 | de la Rama ....... A61B 18/1492 600/374 |
| 8,303,584 B2 | 11/2012 | Burdio Pinilla et al. |
| 8,388,573 B1 | 3/2013 | Cox |
| 8,398,624 B2 | 3/2013 | Rioux et al. |
| 8,409,193 B2 | 4/2013 | Young et al. |
| 8,444,638 B2 | 5/2013 | Woloszko et al. |
| 8,465,484 B2 | 6/2013 | Davalos et al. |
| 8,465,486 B2 * | 6/2013 | Danek ................ A61B 18/1477 606/41 |
| 8,588,886 B2 | 11/2013 | de la Rama et al. |
| 8,591,461 B2 | 11/2013 | Boatman |
| 8,617,158 B2 | 12/2013 | Garabedian et al. |
| 8,647,339 B2 | 2/2014 | Satake |
| 8,657,814 B2 | 2/2014 | Werneth et al. |
| 8,734,439 B2 | 5/2014 | Gough et al. |
| 8,814,855 B2 | 8/2014 | DiCarlo et al. |
| 8,834,461 B2 | 9/2014 | Werneth et al. |
| 8,979,841 B2 | 3/2015 | Kunis et al. |

(56) References Cited

U.S. PATENT DOCUMENTS

| | | |
|---|---|---|
| 9,078,665 B2 | 7/2015 | Moss et al. |
| 2001/0031941 A1 | 10/2001 | Edwards et al. |
| 2002/0026186 A1 | 2/2002 | Woloszko et al. |
| 2002/0087208 A1 | 7/2002 | Koblish et al. |
| 2002/0095152 A1 | 7/2002 | Ciarrocca et al. |
| 2002/0115992 A1 | 8/2002 | Utley et al. |
| 2003/0036680 A1 | 2/2003 | Black |
| 2003/0225403 A1 | 12/2003 | Woloszko et al. |
| 2004/0087936 A1 | 5/2004 | Stern et al. |
| 2005/0154386 A1 | 7/2005 | West et al. |
| 2006/0259027 A1 | 11/2006 | Kwan et al. |
| 2007/0083195 A1 | 4/2007 | Werneth et al. |
| 2008/0004534 A1 | 1/2008 | Gelbart et al. |
| 2008/0103494 A1 | 5/2008 | Rioux et al. |
| 2009/0171340 A1 | 7/2009 | Young |
| 2009/0292177 A1 | 11/2009 | Eggers et al. |
| 2009/0299355 A1 | 12/2009 | Bencini et al. |
| 2010/0114087 A1* | 5/2010 | Edwards ............ A61B 18/1477 606/33 |
| 2011/0172485 A1 | 7/2011 | Lubock |
| 2011/0257646 A1 | 10/2011 | Utley et al. |
| 2012/0029510 A1* | 2/2012 | Haverkost .......... A61B 18/1492 606/41 |
| 2012/0109250 A1 | 5/2012 | Cates et al. |
| 2013/0085493 A1 | 4/2013 | Bloom et al. |
| 2013/0158536 A1* | 6/2013 | Bloom ............... A61B 18/1492 606/33 |
| 2013/0172870 A1 | 7/2013 | Germain et al. |
| 2013/0184702 A1 | 7/2013 | Neal, II et al. |
| 2013/0253506 A1 | 9/2013 | Rioux et al. |
| 2014/0018794 A1 | 1/2014 | Anderson et al. |
| 2014/0031810 A1 | 1/2014 | Mahvi et al. |
| 2014/0276748 A1* | 9/2014 | Ku ....................... A61B 18/18 606/33 |
| 2015/0141982 A1 | 5/2015 | Lee |
| 2016/0113708 A1 | 4/2016 | Moss et al. |
| 2016/0184008 A1 | 6/2016 | Papaioannou et al. |
| 2016/0317221 A1 | 11/2016 | Rioux |
| 2017/0000559 A1 | 1/2017 | Rioux et al. |
| 2017/0119454 A1 | 5/2017 | Rioux et al. |

FOREIGN PATENT DOCUMENTS

| | | |
|---|---|---|
| EP | 0777445 B1 | 6/1999 |
| EP | 2942023 A3 | 2/2016 |
| JP | 3009735 B2 | 2/2000 |
| WO | 9510326 A1 | 4/1995 |
| WO | 9942047 A1 | 8/1999 |
| WO | 0051683 A1 | 9/2000 |
| WO | 2012015722 A1 | 2/2012 |
| WO | 2014022379 A1 | 2/2014 |
| WO | 2015/142674 A1 | 9/2015 |

OTHER PUBLICATIONS

"Starburst Talon" Specifications Brochure, Angiodynamics, 2013 (2 Pages).

Medtronic, "Aquamantys Bipolar Sealers." Electrosurgical Products, Jun. 2017. Retrieved Jul. 21, 2017. <http://www.medtronic.com/us-en/healthcare-professionals/products/general-surgery/electrosurgical/aquamantys-bipolar-sealers.html> (11 Pages).

Extended European Search Report dated Jun. 10, 2016 for European Application No. 13825361.2 (13 Pages).

International Search Report and Written Opinion of the International Searching Authority dated Aug. 22, 2016 for International Application No. PCT/US2016/030081 (11 Pages).

International Search Report and Written Opinion of the International Searching Authority dated Aug. 5, 2015 for International Application No. PCT/US2015/020596 (13 Pages).

International Search Report and Written Opinion of the International Searching Authority dated Feb. 2, 2017 for International Application No. PCT/US2016/059345 (10 Pages).

International Search Report and Written Opinion of the International Searching Authority dated May 16, 2017 for International Application No. PCT/US2017/015582 (11 pages).

International Search Report and Written Opinion of the International Searching Authority dated May 16, 2017 for International Application No. PCT/US2017/015584 (11 pages).

International Search Report and Written Opinion of the International Searching Authority dated Nov. 29, 2013 for International Application No. PCT/US2013/052703 (11 Pages).

International Search Report and Written Opinion of the International Searching Authority dated Jun. 11, 2017 for International Application No. PCT/US2017/019398 (27 Pages).

Non-Final Office Action dated Aug. 11, 2017 for U.S. Appl. No. 15/337,334 (11 Pages).

Response to Non-Final Office Action Filed Sep. 20, 2017 for U.S. Appl. No. 15/337,334 (6 Pages).

Non-Final Office Action dated Aug. 4, 2017 for U.S. Appl. No. 15/624,230 (18 Pages).

Response to Non-Final Office Action Filed Sep. 20, 2017 for U.S. Appl. No. 15/624,230 (10 Pages).

International Search Report and Written Opinion of the International Searching Authority dated Oct. 19, 2017 for International Application No. PCT/US2017/041501 (63 pages).

\* cited by examiner

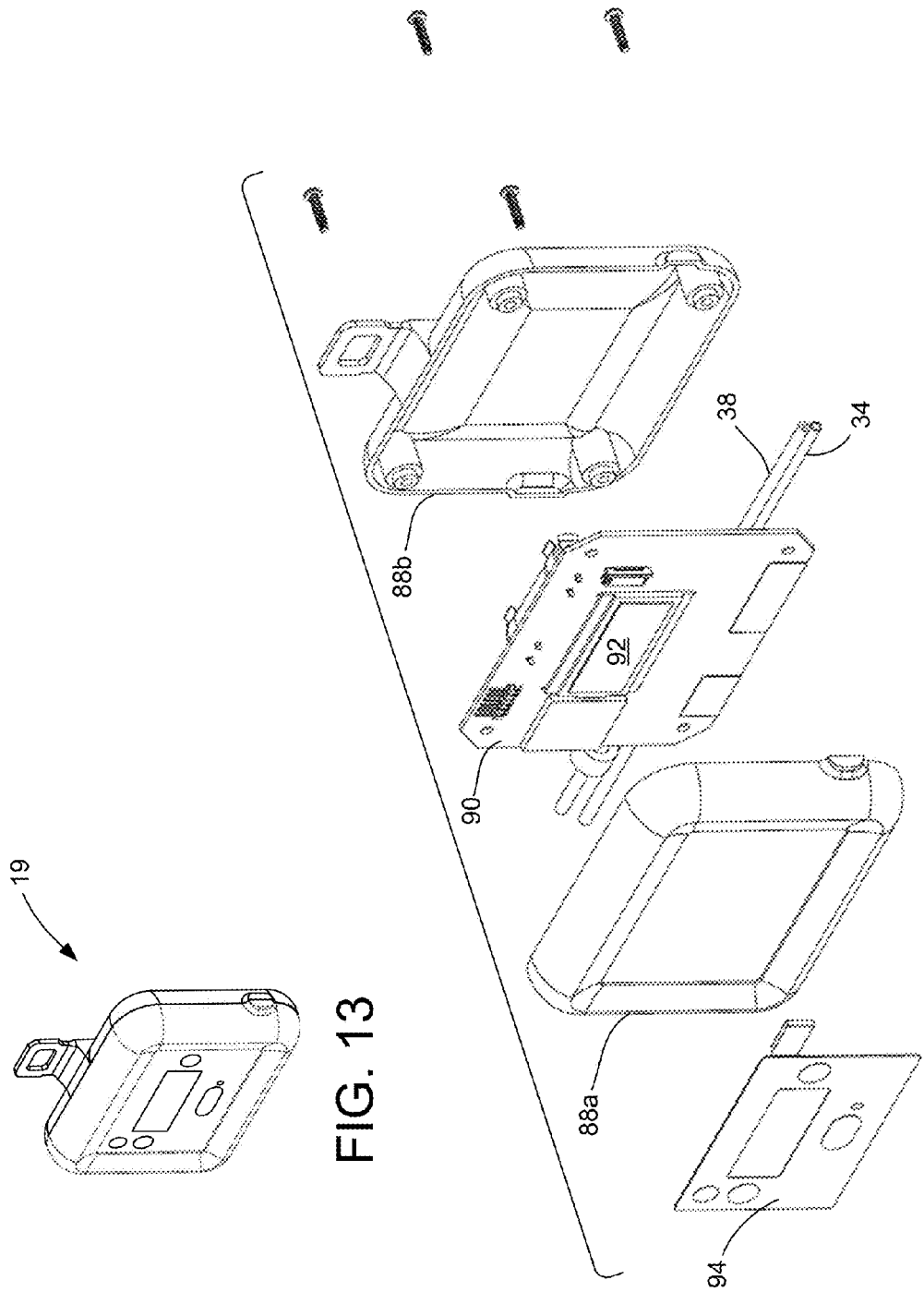

SCREEN SPHERE TISSUE ABLATION DEVICES AND METHODS

CROSS-REFERENCE TO RELATED APPLICATIONS

This application is a continuation of U.S. Non-Provisional application Ser. No. 15/337,334, filed Oct. 28, 2016, which claims the benefit of, and priority to, U.S. Provisional Application No. 62/248,157, filed Oct. 29, 2015, and U.S. Provisional Application No. 62/275,984, filed Jan. 7, 2016, the contents of each of which are hereby incorporated by reference herein in their entirety.

FIELD

The present disclosure relates generally to medical devices, and, more particularly, to screen sphere tissue ablation devices and methods for ablation of marginal tissue surrounding a tissue cavity.

BACKGROUND

Cancer is a group of diseases involving abnormal cell growth with the potential to invade or spread to other parts of the body. Cancer generally manifests into abnormal growths of tissue in the form of a tumor that may be localized to a particular area of a patient's body (e.g., associated with a specific body part or organ) or may be spread throughout. Tumors, both benign and malignant, are commonly treated and removed via surgical intervention, as surgery often offers the greatest chance for complete removal and cure, especially if the cancer has not spread to other parts of the body. Electrosurgical methods, for example, can be used to destroy these abnormal tissue growths. However, in some instances, surgery alone is insufficient to adequately remove all cancerous tissue from a local environment.

For example, treatment of early stage breast cancer typically involves a combination of surgery and adjuvant irradiation. Unlike a mastectomy, a lumpectomy removes only the tumor and a small rim (area) of the normal tissue around it. Radiation therapy is given after lumpectomy in an attempt to eradicate cancer cells that may remain in the local environment around the removed tumor, so as to lower the chances of the cancer returning. However, radiation therapy as a post-operative treatment suffers various shortcomings. For example, radiation techniques can be costly and time consuming, and typically involve multiple treatments over weeks and sometimes months. Furthermore, radiation often results in unintended damage to the tissue outside the target zone. Thus, rather than affecting the likely residual tissue, typically near the original tumor location, radiation techniques often adversely affect healthy tissue, such as short and long-term complications affecting the skin, lungs, and heart.

Accordingly, such risks, when combined with the burden of weeks of daily radiation, may drive some patients to choose mastectomy instead of lumpectomy. Furthermore, some women (e.g., up to thirty percent (30%)) who undergo lumpectomy stop therapy before completing the full treatment due to the drawbacks of radiation treatment. This may be especially true in rural areas, or other areas in which patients may have limited access to radiation facilities.

SUMMARY

Tumors, both benign and malignant, are commonly treated and destroyed via surgical intervention, as surgery often offers the greatest chance for complete removal and cure, especially if the cancer has not metastasized. However, after the tumor is destroyed, a hollow cavity may remain, wherein tissue surrounding this cavity and surrounding the original tumor site can still leave abnormal or potentially cancerous cells that the surgeon fails, or is unable, to excise. This surrounding tissue is commonly referred to as "margin tissue" or "marginal tissue", and is the location within a patient where a reoccurrence of the tumor may most likely occur.

The systems and methods described herein can be used during an ablation procedure to destroy a thin rim of normal tissue around the cavity in an effort to manage residual disease in the local environment that has been treated. This technique can help to ensure that all microscopic disease in the local environment has been treated. This is especially true in the treatment of tumors that have a tendency to recur. Applications of such a method of intra-operatively extending tumor margins are applicable to many areas of the body including the liver and especially the breast.

In particular, the present disclosure is generally directed to a cavitary tissue ablation system including an ablation device to be delivered into a tissue cavity and emit non-ionizing radiation, such as radiofrequency (RF) energy, to treat the marginal tissue around the tissue cavity. The tissue ablation device of the present invention generally includes a probe including an elongated shaft configured as a handle and adapted for manual manipulation and a nonconductive distal portion coupled to the shaft. The nonconductive distal portion includes an electrode array positioned along an external surface thereof. The distal portion, including the electrode array, can be delivered to and maneuvered within a tissue cavity (e.g., formed from tumor removal) and configured to ablate marginal tissue (via RF energy) immediately surrounding the tissue cavity in order to minimize recurrence of the tumor.

In one aspect, the electrode array is composed of a plurality of conductive members (e.g., conductive wires) electrically isolated and independent from one another. Thus, in some embodiments, each of the plurality of conductive wires, or one or more sets of a combination of conductive wires, is configured to independently receive an electrical current from an energy source (e.g., ablation generator) and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wires) can function as a ground or neutral conductive member.

The independent control of each wire or sets of wires allows for activation (e.g., emission of RF energy) of corresponding portions of the electrode array. For example, the electrode array may be partitioned into specific portions which may correspond to clinical axes or sides of the distal portion of the device. In one embodiment, the electrode array may include at least four distinct portions (i.e., individual or sets of conductive wires) corresponding to four clinical axes or sides of the distal portion (e.g, four sides or quadrants around spheroid body).

In some embodiments, the ablation device is configurd to provide RF ablation via a virtual electrode arrangement, which includes distribution of a fluid along an exterior surface of the distal tip and, upon activation of the electrode array, the fluid may carry, or otherwise promote, energy emitted from the electrode array to the surrounding tissue. For example, the nonconductive distal portion of the ablation device includes an interior chamber retaining at least a spacing member (e.g., spacer ball) and a hydrophilic insert surrounding a spacing member. The interior chamber of the distal portion is configured to receive and retain a fluid (e.g., saline) therein from a fluid source. The hydrophilic insert is configured receive and evenly distribute the fluid through the distal tip by wicking the saline against gravity. The distal portion may generally include a plurality of ports or apertures configured to allow the fluid to pass therethrough, or weep, from the interior chamber to an external surface of the distal portion. The spacer member is shaped and sized so as to maintain the hydrophilic insert in contact with the interior surface of the distal tip wall, and specifically in contact with the one or more perforations, such that the hydrophilic insert provides uniformity of saline distribution to the perforations. Accordingly, upon positioning the distal portion within a target site (e.g., tissue cavity to be ablated), the electrode array can be activated. The fluid weeping through the perforations to the outer surface of the distal portion is able to carry energy from electrode array, thereby creating a virtual electrode. Accordingly, upon the fluid weeping through the perforations, a pool or thin film of fluid is formed on the exterior surface of the distal portion and is configured to ablate surrounding tissue via the RF energy carried from the electrode array.

It should be noted the devices and methods of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., lungs, liver, pancreas, etc.) and is not limited to treatment of breast cancer.

BRIEF DESCRIPTION OF THE DRAWINGS

Features and advantages of the claimed subject matter will be apparent from the following detailed description of embodiments consistent therewith, which description should be considered with reference to the accompanying drawings, wherein:

FIGS. 13 and 14 are perspective and exploded perspective views, respectively, of one embodiment of a device controller consistent with the present disclosure;

Figure 1:
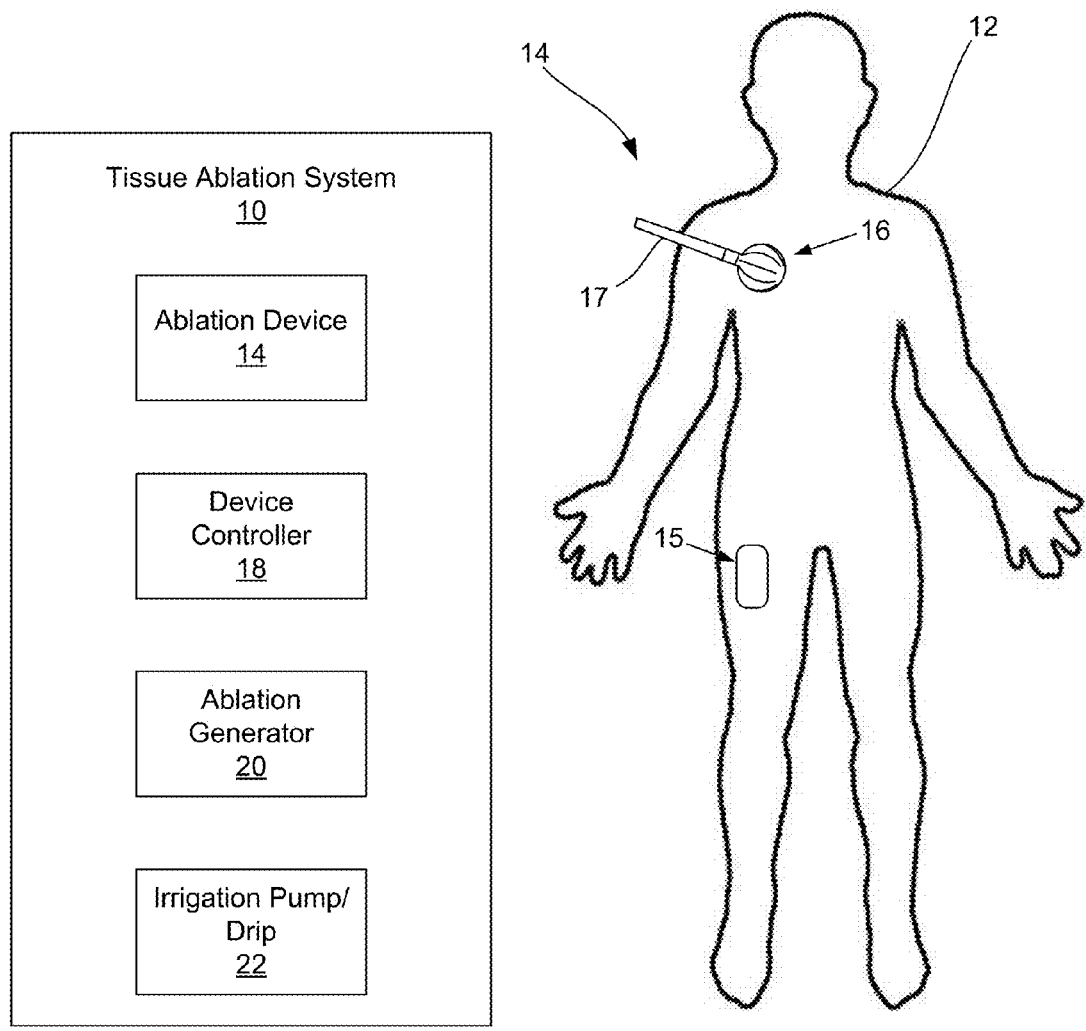
FIG. 1 is a schematic illustration of an ablation system consistent with the present disclosure.

For a thorough understanding of the present disclosure, reference should be made to the following detailed description, including the appended claims, in connection with the above-described drawings. Although the present disclosure is described in connection with exemplary embodiments, the disclosure is not intended to be limited to the specific forms set forth herein. It is understood that various omissions and substitutions of equivalents are contemplated as circumstances may suggest or render expedient.

DETAILED DESCRIPTION

By way of overview, the present disclosure is generally directed to a tissue ablation device having a deployable applicator head configured to be delivered into a tissue cavity and ablate marginal tissue surrounding the tissue cavity.

A tissue ablation system consistent with the present disclosure may be well suited for treating hollow body cavities, such as irregularly-shaped cavities in breast tissue created by a lumpectomy procedure. For example, once a tumor has been removed, a tissue cavity remains. The tissue surrounding this cavity is the location within a patient where a reoccurrence of the tumor may most likely occur. Consequently, after a tumor has been removed, it is desirable to destroy the surrounding tissue (also referred herein as the "margin tissue" or "marginal tissue").

The tissue ablation system of the present disclosure can be used during an ablation procedure to destroy the thin rim of marginal tissue around the cavity in a targeted manner. In particular, the present disclosure is generally directed to a cavitary tissue ablation system including an ablation device to be delivered into a tissue cavity and configured to emit non-ionizing radiation, such as radiofrequency (RF) energy, in a desired shape or pattern so as to deliver treatment for the ablation and destruction of a targeted portion of marginal tissue around the tissue cavity.

The tissue ablation device of the present invention generally includes a probe including an elongated shaft configured as a handle and adapted for manual manipulation and a nonconductive distal portion coupled to the shaft. The nonconductive distal portion includes an electrode array positioned along an external surface thereof. The distal portion, including the electrode array, can be delivered to and maneuvered within a tissue cavity (e.g., formed from tumor removal) and configured to ablate marginal tissue (via RF energy) immediately surrounding the tissue cavity in order to minimize recurrence of the tumor. The tissue ablation device of the present disclosure is configured to allow surgeons, or other medical professionals, to deliver precise, measured doses of RF energy at controlled depths to the marginal tissue surrounding the cavity.

Accordingly, a tissue ablation device consistent with the present disclosure may be well suited for treating hollow body cavities, such as irregularly-shaped cavities in breast tissue created by a lumpectomy procedure. It should be noted, however, that the devices of the present disclosure are not limited to such post-surgical treatments and, as used herein, the phrase "body cavity" may include non-surgically created cavities, such as natural body cavities and passages, such as the ureter (e.g. for prostate treatment), the uterus (e.g. for uterine ablation or fibroid treatment), fallopian tubes (e.g. for sterilization), and the like. Additionally, or alternatively, tissue ablation devices of the present disclosure may be used for the ablation of marginal tissue in various parts of the body and organs (e.g., skin, lungs, liver, pancreas, etc.) and is not limited to treatment of breast cancer.

FIG. 1 is a schematic illustration of an ablation system 10 for providing targeted ablation of marginal tissue during a tumor removal procedure in a patient 12. The ablation system 10 generally includes an ablation device 14, which includes a probe having a distal tip or portion 16 and an elongated catheter shaft 17 to which the distal tip 16 is connected. The catheter shaft 17 may generally include a nonconductive elongated member including a fluid delivery lumen. The ablation device 14 may further be coupled to a device controller 18 and an ablation generator 20 over an electrical connection (electrical line 34 shown in FIG. 2), and an irrigation pump or drip 22 over a fluid connection (fluid line 38 shown in FIG. 2). The ablation generator 20 may also connected to a return electrode 15 that is attached to the skin of the patient 12.

As will be described in greater detail herein, the device controller 18 may be used to control the emission of energy from one or more conductive members of the device 14 to result in ablation, as well as controlling the delivery of fluid to the applicator head 16 so as to control subsequent weeping of fluid from the head 16 during an RF ablation procedure. In some cases, the device controller 18 may be housed within the ablation device 14. The ablation generator 20 may also connected to a return electrode 15 that is attached to the skin of the patient 12.

As will be described in greater detail herein, during an ablation treatment, the ablation generator 20 may generally provide RF energy (e.g., electrical energy in the radiofrequency (RF) range (e.g., 350-800 kHz)) to an electrode array of the ablation device 14, as controlled by the device controller 18. At the same time, saline may also be released from the head 16. The RF energy travels through the blood and tissue of the patient 12 to the return electrode 15 and, in the process, ablates the region(s) of tissues adjacent to portions of the electrode array that have been activated.

Figure 2:
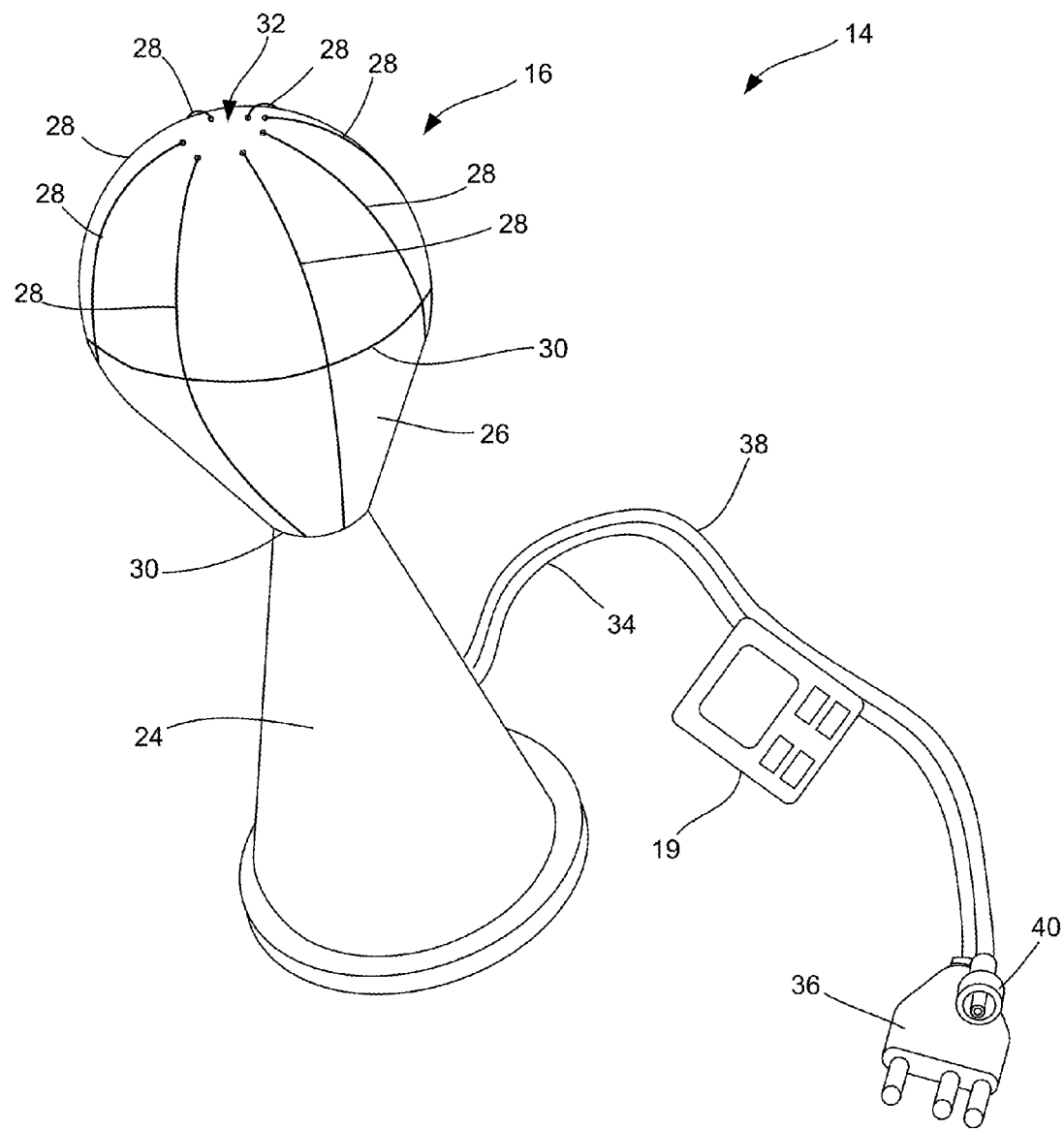
FIG. 2 is a perspective view of an ablation device tip of the ablation system of FIG. 1.

FIG. 2 is a perspective view of the distal portion or tip 16 of the ablation device 14. The distal tip 16 may include a neck portion 24 and a generally spheroid body 26 extending distally from the neck 24. It should be noted that, in some embodiments, the spheroid body 26 may be generally rigid and may maintain a default shape. However, in some embodiments, the spheroid body 26 may be configured to transition between a collapsed state and an expanded state, as will be described in greater detail herein, particular with respect to FIGS. 5A-5B and 6-7. For example, the spheroid body 26 may be collapsible to a delivery configuration having a reduced size (e.g., equatorial diameter) relative to the deployed configuration size (e.g., equatorial diameter) of the spheroid body 26.

In some examples, the spheroid body 26 includes a non-conductive material (e.g., a polyamide) as a layer on at least a portion of an internal surface, an external surface, or both an external and internal surface. In other examples, the spheroid body 26 is formed from a non-conductive material. Additionally or alternatively, the spheroid body 26 material can include an elastomeric material or a shape memory material.

In some examples, the spheroid body 26 has a diameter (e.g., an equatorial diameter) of about 80 mm or less. In certain implementations, the spheroid body 26 of the distal tip, in a deployed configuration, has an equatorial diameter of 2.0 mm to 60 mm (e.g., 5 mm, 10 mm, 12 mm, 16 mm, 25 mm, 30 mm, 35 mm, 40 mm, 50 mm, and 60 mm). Based on the surgical procedure, the collapsibility of the spheroid body 26 can enable the distal tip to be delivered using standard sheaths (e.g., an 8F introducer sheath). However, the spheroid body 26 need not be collapsible in some procedures, and thus has a relatively rigid body and maintains the default shape.

The distal tip 16 of the ablation device 14 further includes an electrode array positioned thereon. The electrode array includes at least one conductive member 28. As illustrated in the figures, the electrode array may includes at least eight conductive members 28. Accordingly, the electrode array may include a plurality of conductive members 28. The plurality of conductive members 28 extend within the distal tip 16, through a channel 32 and along an external surface of the spheroid body 26. The conductive members 28 extend along the longitudinal length of the distal tip 16 and are radially spaced apart (e.g., equidistantly spaced apart) from each other. These conductive members transmit RF energy from the ablation generator and can be formed of any suitable conductive material (e.g., a metal such as stainless steel, nitinol, or aluminum). In some examples, the conductive members 28 are metal wires. Accordingly, for ease of description, the conductive member(s) will be referred to hereinafter as "conductive wire(s) 28".

As illustrated, one or more of the conductive wires 28 can be electrically isolated from one or more of the remaining conductive wires 28. This electrical isolation enables various operation modes for the ablation device 14. For example, ablation energy may be supplied to one or more conductive wires 28 in a bipolar mode, a unipolar mode, or a combination bipolar and unipolar mode. In the unipolar mode, ablation energy is delivered between one or more conductive wires 28 on the ablation device 14 and the return electrode 15, as described with reference to FIG. 1. In bipolar mode, energy is delivered between at least two of the conductive wires 28, while at least one conductive wire 28 remains neutral. In other words, at least, one conductive wire functions as a grounded conductive wire (e.g., electrode) by not delivering energy over at least one conductive wire 28.

The electrode array may further include one or more stabilizing members 30 configured to provide support for the plurality of conductive wires 28. The one or more stabilizing member 30 generally extend along a surface (e.g., external or internal) of the distal tip 16 so as to circumscribe the spheroid body 26. The stabilizing members 30 can, in some examples, electrically connect to one or more conductive wires 28. In other examples, the stabilizing members 30 are non-conductive. The stabilizing members 30 can be formed of a suitably stiff material (e.g., metal such as stainless steel, nitinol, or aluminum). In some implementations, the stabilizing members 30 can be integral with a portion of the spheroid body 26 (e.g., as a rib). While, the distal tip 16 is generally shown with one or more stabilizing members, in some implementations, the distal tip 16 is free of stabilizing members.

Figures 4A, 4B:
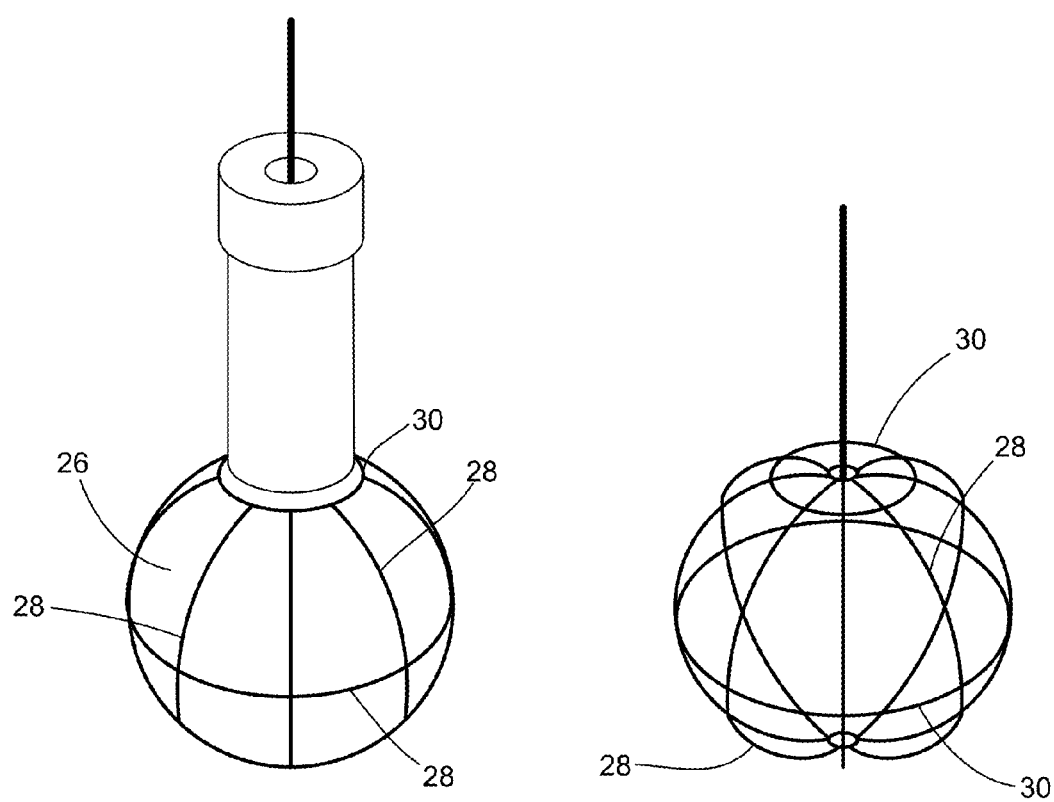
FIGS. 4A and 4B schematically illustrate the ablation device tip of the ablation device of FIG. 1 with and without the nonconductive distal portion, respectively.

To further aid in illustrating the arrangement of the conductive wires 28 and the non-conductive spheroid body 26, FIG. 4A shows the conductive wires 28 positioned over the non-conductive spheroid body 26 while FIG. 4B shows the electrode array of the ablation device without the non-conductive spheroid body 26.

As shown, the distal tip 16 may be coupled to the ablation generator 20 and/or irrigation pump 22 via an electrical line 34 and a fluid line 38, respectively. Each of the electrical line 34 and fluid line 38 may include an adaptor end 36, 40, respectively, configured to couple the associated lines with a respective interface on the ablation generator 20 and irrigation pump 22. In some examples, the ablation device 14 may further include a user switch or interface 19 which may serve as the device controller 18 and thus, may be in electrical communication with the ablation generator 20 and the ablation device 14, as well as the irrigation pump 22 for controlling the amount of fluid to be delivered to the tip 16.

The switch 19 can provide a user with various options with respect to controlling the ablation output of the device 14, as will be described in greater detail herein. For example, the switch 19, which may serve as the device controller 18, may include a timer circuit, or the like, to enable the conductive wires 28 to be energized for a pre-selected or desired amount of time. After the pre-selected or desired amount of time elapses, the electrical connection can be automatically terminated to stop energy delivery to the patient. In some cases, the switch 19 may be connected to individual conductive wires 28. For example, in some embodiments, the switch 19 may be configured to control energy delivery from the ablation generator 20 so that one or more individual conductive wires, or a designated combination of conductive wires, are energized for a pre-selected, or desired, duration.

Figure 3A:
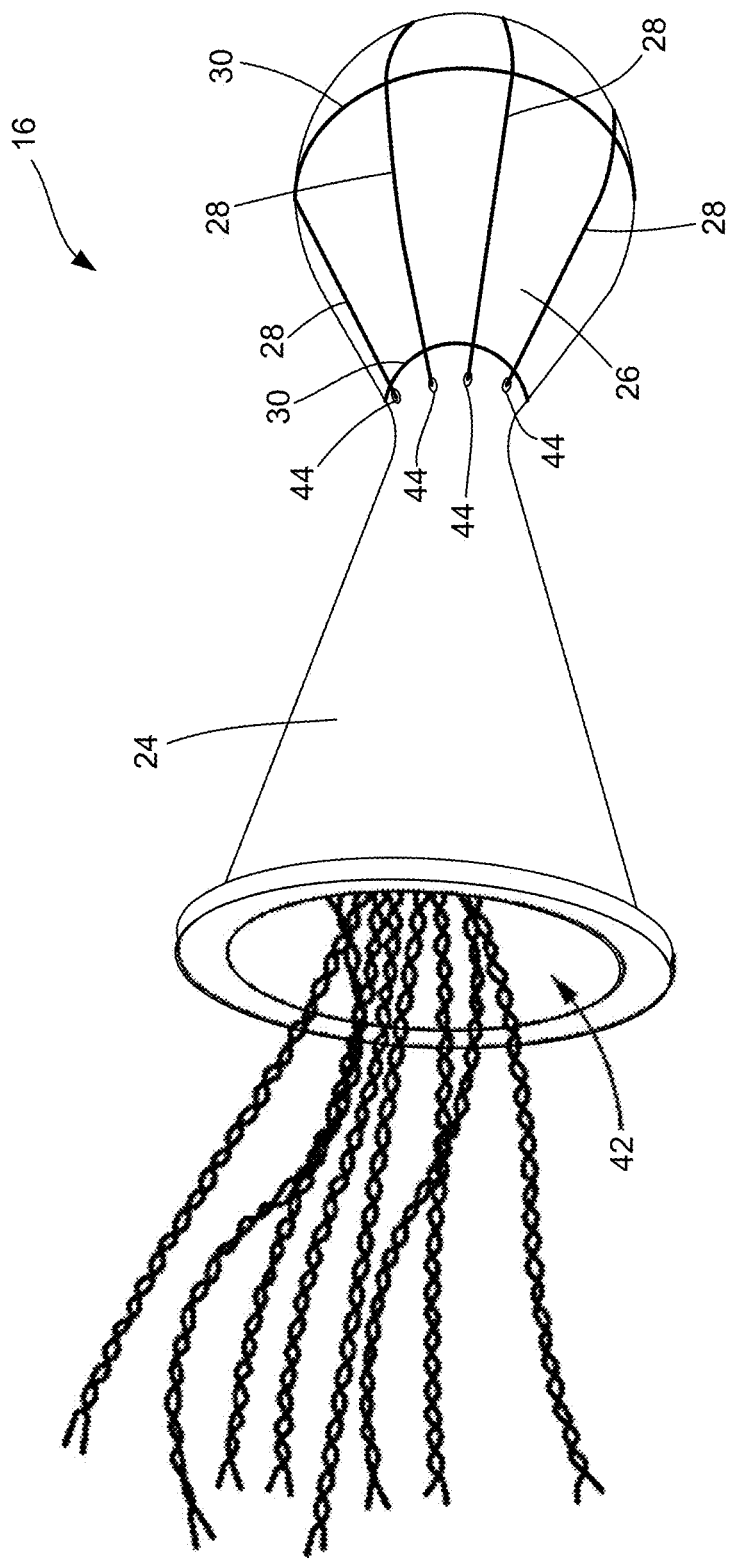
FIGS. 3A, 3B, and 3C are perspective views of the ablation device tip of FIG. 2 in greater detail.
Figure 3B:
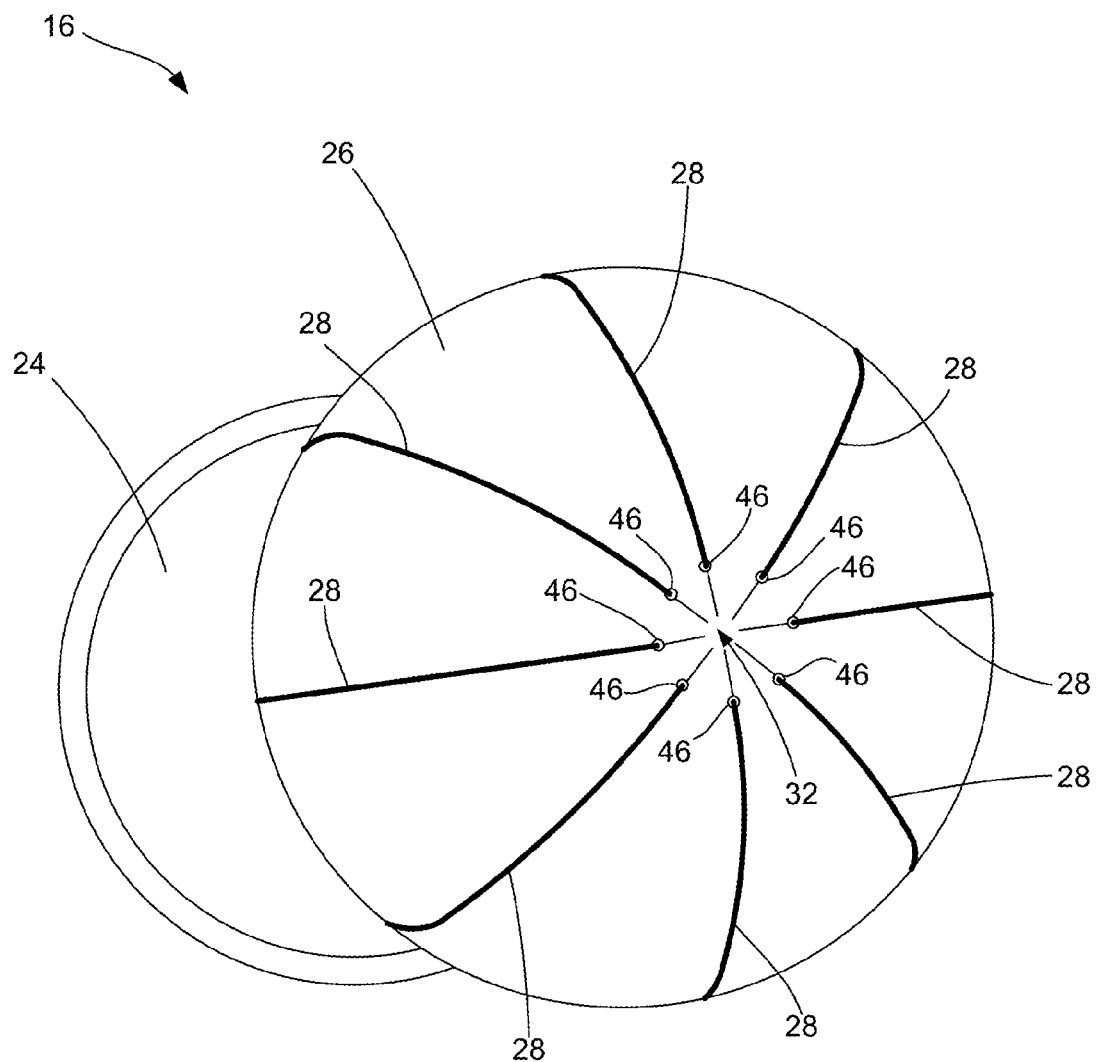
Figure 3C:
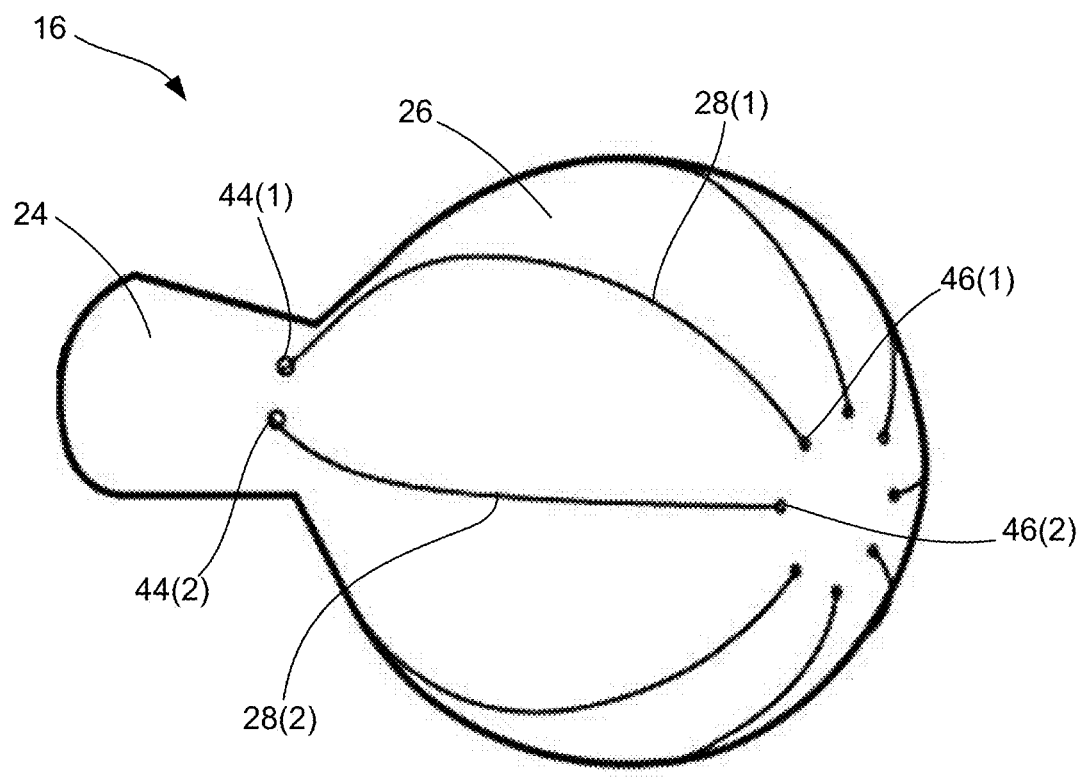

FIGS. 3A, 3B, and 3C are perspective views of the distal tip 16 of FIG. 2 in greater detail. As shown in FIGS. 2 and 3A-3C, the conductive wires 28 extend through a lumen 42 within the distal tip 16. For example, each of the conductive wires 28 enters the lumen 42 of the neck 27 and extends through the distal tip portion 16 before exiting the distal tip through either a center channel 32 at a distal most portion of the distal tip or one of a plurality of proximal ports 44. In some examples, a plurality of distal ports 46 extending through a wall of the distal tip 16 is positioned around the channel 32. A plurality of proximal ports 44 can also extend through a wall of the distal tip 16. These proximal ports 44 can be positioned around the distal tip 16 in close proximity (e.g., within at least 5 mm, within at least 3 mm, within at least 1 mm, within 0.5 mm, within 0.4 mm, or within 0.2 mm) to the junction between the spheroidal body 26 and the neck 24 of the distal tip 16. In some cases, the number of proximal ports 44 and distal ports 46 is equal to the number of conductive wires 28.

In some examples, each conductive wire 28 can extend through a different distal port 46, which allows the conductive wires 28 to remain electrically isolated from one another. In other examples, one or more conductive wires can extend through the same distal port 46.

Upon passing through a distal port 46, each conductive wire 28 can extend along an external surface of the distal tip 16. In some examples, the length of the conductive wire 28 extending along the external surface is at least 20% (e.g., at least, 50%, 60%, 75%, 85%, 90%, or 99%) of the length of the spheroid body 26. The conductive wire 28 can then re-enter the lumen 42 of the distal tip 16 through a corresponding proximal port 44. For example, as shown in FIG. 3C, conductive wire 28(1) passes through distal port 46(1), extends along a length of the external surface of the distal tip 16, and passes through an associated proximal port 44(1) into the lumen 42 of the distal tip 16, while conductive wire 28(2) is electrically isolated from conductive wire 28(1) in that it passes through associated proximal and distal ports 44(2), 46(2), respectively.

In some examples, each conductive wire 28 can extend through a different associated proximal port 44, which allows the conductive wires 28 to remain electrically isolated from one another. In other examples, one or more conductive wires can extend through the same proximal port. Yet still, as will be described in greater detail herein, particularly with reference to the device 14*a* illustrated in FIGS. 18A-18B and 19A-19B, an individual conductive wire can extend through multiple proximal and distal ports.

Figure 5B:
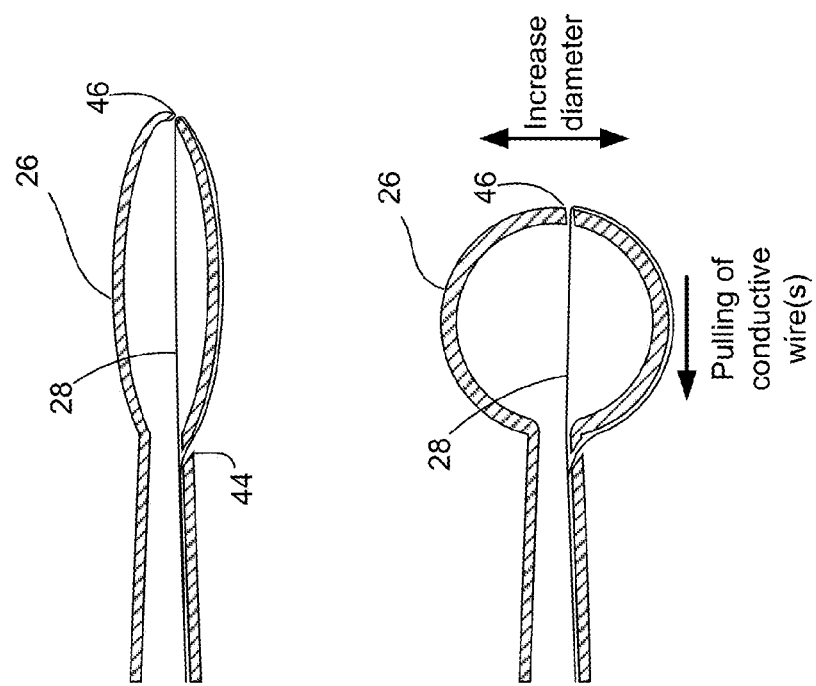
FIG. 5A is a side view and FIG. 5B is a cross-sectional view of one embodiment of a deployable distal portion of the ablation device illustrating transitioning of the distal portion from a delivery configuration to a deployed configuration.
Figure 5A:
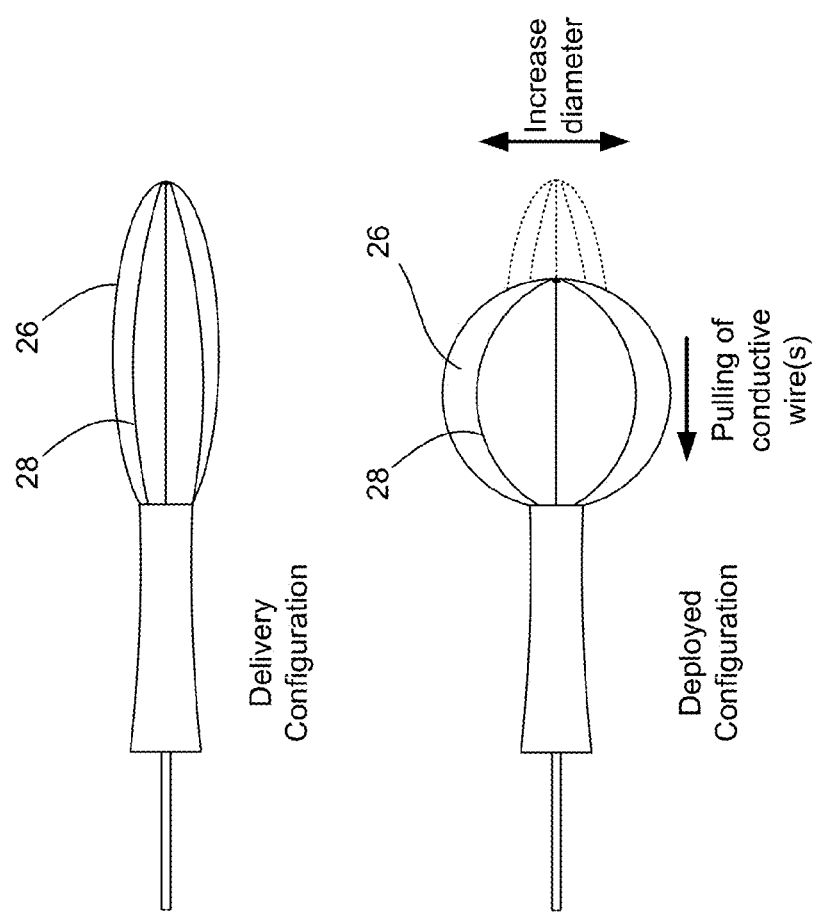

In some embodiments, the spheroid body 26 may be configured to transition between a collapsed state and an expanded state, which may allow for a surgeon to introduce the distal portion 26 into certain areas of the body that may have reduced openings and could be difficult to access with when the spheroid body is in the default shape. FIG. 5A is a side view and FIG. 5B is a cross-sectional view of one embodiment of a deployable distal portion 26 of the ablation device 14 illustrating transitioning of the distal portion 26 from a delivery configuration to a deployed configuration.

As shown, when in a delivery configuration, the spheroid body 26 may generally have a prolate-spheroid shape, thereby having a reduced size (e.g., equatorial diameter) relative to the deployed configuration size (e.g., equatorial diameter). In some embodiments, the spheroid body 26 may be configured to transition between the delivery and deployed configurations via manipulation of one or more of the conductive wires. For example, as shown in FIG. 5B, at least one conductive wire 28 may be configured to translate axially along a longitudinal axis of the distal tip 16, which, in turn, can exert a force on at least a region of the distal tip 16 that causes or partially causes the spheroid body 26 to transition or deform between a delivery configuration to a deployed configuration. For example, axial translation of the conductive wire 28 along an axial direction exerts a force on the distal tip 16, which causes spheroid body 26 to assume a more spherical configuration for deployment. In other words, axially translating the conductive wire 28 causes the spheroid body 26 to transition from a delivery configuration in which the spheroid body 26 exhibits a prolate-spheroid shape to a deployment configuration in which the spheroid body 26 exhibits an oblate-spheroid shape.

Figure 6:
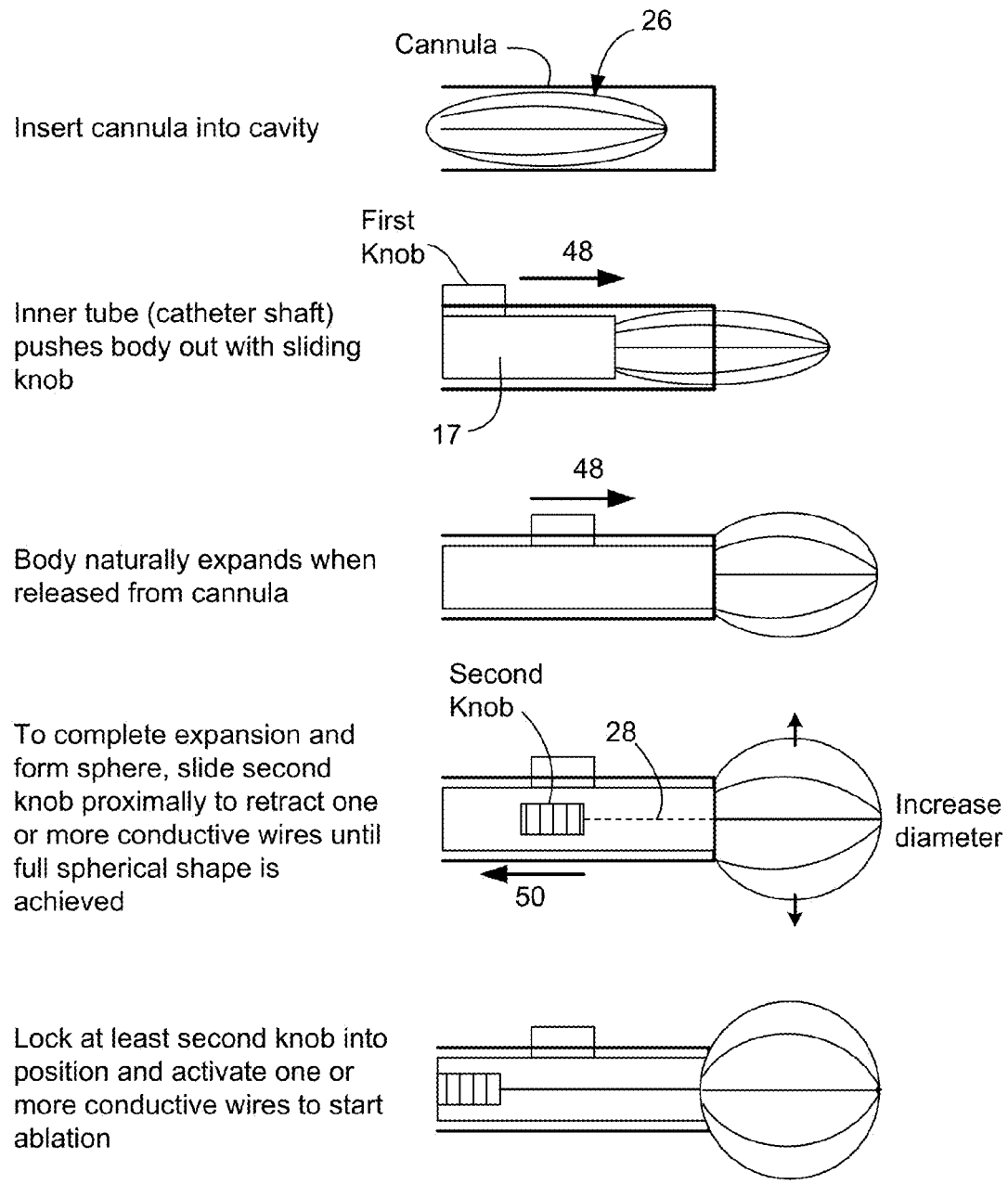
FIG. 6 illustrates a method of deploying the distal portion of FIGS. 5A and 5B into an expanded configuration for delivery of RF energy to a target site for ablation of marginal tissue.

FIG. 6 illustrates a method of deploying the distal portion 16 into an expanded configuration for delivery of RF energy to a target site for ablation of marginal tissue. As shown, the catheter shaft 17 of the ablation device 14 can optionally include a dedicated control wire connected to a knob or control mechanism accessible on the catheter shaft. In this example, one or more control wires or other components may be coupled to the conductive wires to control the retraction and expansion (e.g., via pushing along direction 48 and pulling along direction 50) of the distal tip 105 from the catheter shaft 107. In addition, other components (e.g., electrical wiring for electrically coupling the conductive element and RF generator) can also be housed within the, at least, one lumen of the catheter shaft 17 of the ablation device 14.

In some implementations, the catheter shaft 17 can be configured as a handle adapted for manual manipulation. In some examples, the catheter shaft 17 is additionally or alternatively configured for connection to and/or interface with a surgical robot, such as the Da Vinci® surgical robot available from Intuitive Surgical, Inc., Sunnyvale, Calif. The catheter shaft 17 may be configured to be held in place by a shape lock or other deployment and suspension system of the type that is anchored to a patient bed and which holds the device in place while the ablation or other procedure takes place, eliminating the need for a user to manually hold the device for the duration of the treatment.

Figure 7:
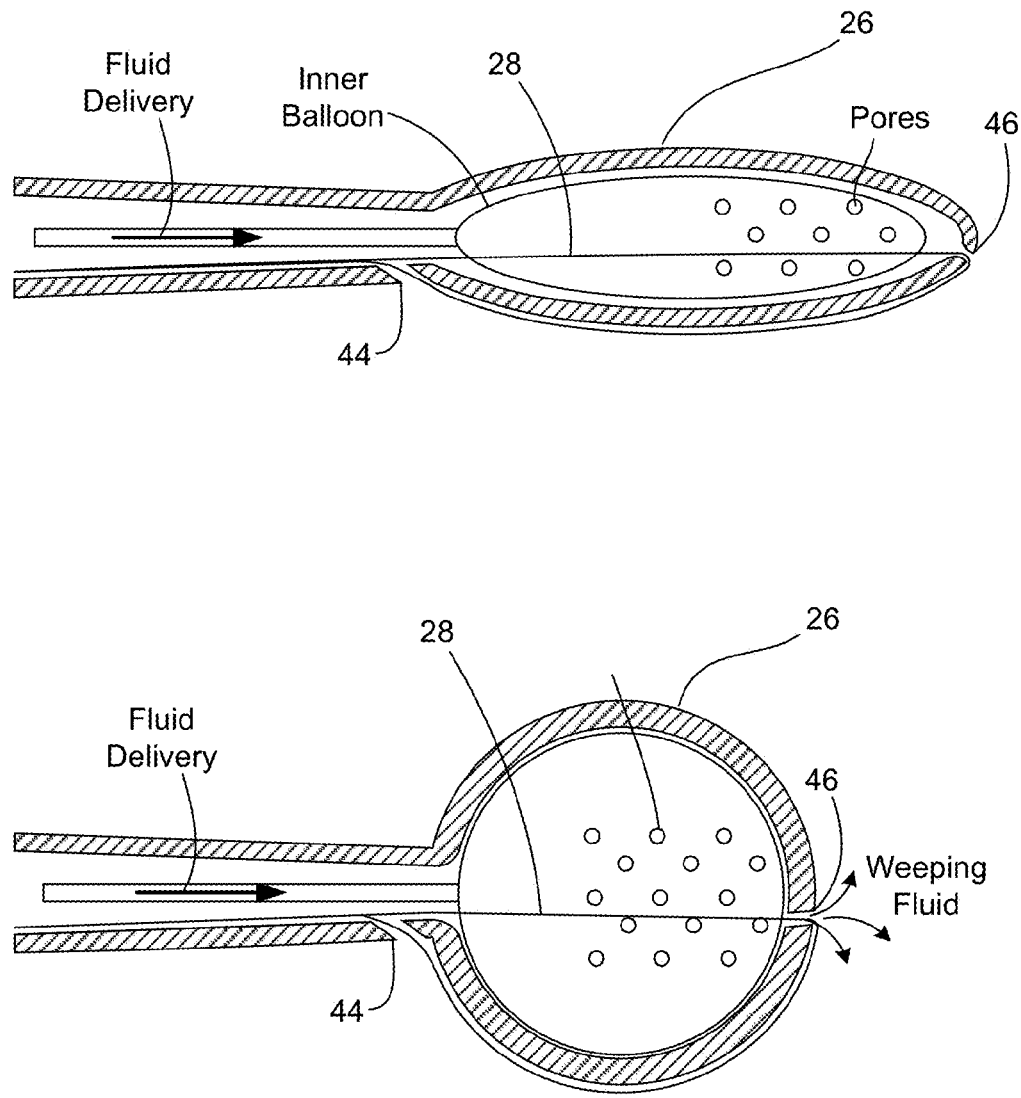
FIG. 7 is a cross-sectional view of the deployable distal portion of FIGS. 5A and 5B illustrating the inclusion of an internal balloon member within an interior chamber of the distal portion. The internal balloon is configured to receive a fluid from a fluid source and thereby expand, which, in turn, causes the distal portion to transition from the delivery configuration to the deployed configuration, and further supply the fluid to an exterior surface of the distal portion, via weeping of the fluid through one or more perforations on the distal portion wall, to create a virtual electrode arrangement with the electrode array.

FIG. 7 is a cross-sectional view of the deployable distal portion of FIGS. 5A and 5B illustrating the inclusion of an internal balloon member within an interior chamber of the distal portion 26. The internal balloon is configured to receive a fluid from a fluid source and thereby expand, which, in turn, causes the distal portion to transition from the delivery configuration to the deployed configuration, and further supply the fluid to an exterior surface of the distal portion, via weeping of the fluid through one or more perforations on the distal portion wall (e.g., distal port 46), to create a virtual electrode arrangement with the electrode array. For example, the inner balloon may include a plurality of perforations, holes, or micropores in the balloon wall so as to allow a fluid provided within the balloon (e.g., saline) to pass therethrough, or weep, from the balloon when the balloon is inflated. The perforations may be sized, shaped, and/or arranged in such a pattern so as to allow a volume of fluid to pass from the interior volume of the balloon into the interior chamber of the distal portion 26 and then to pass through one or more perforations, holes, or micropores formed in the distal portion wall to an exterior surface of the tip at a controlled rate so as to allow the balloon to remain inflated and maintain its shape.

Figure 8:
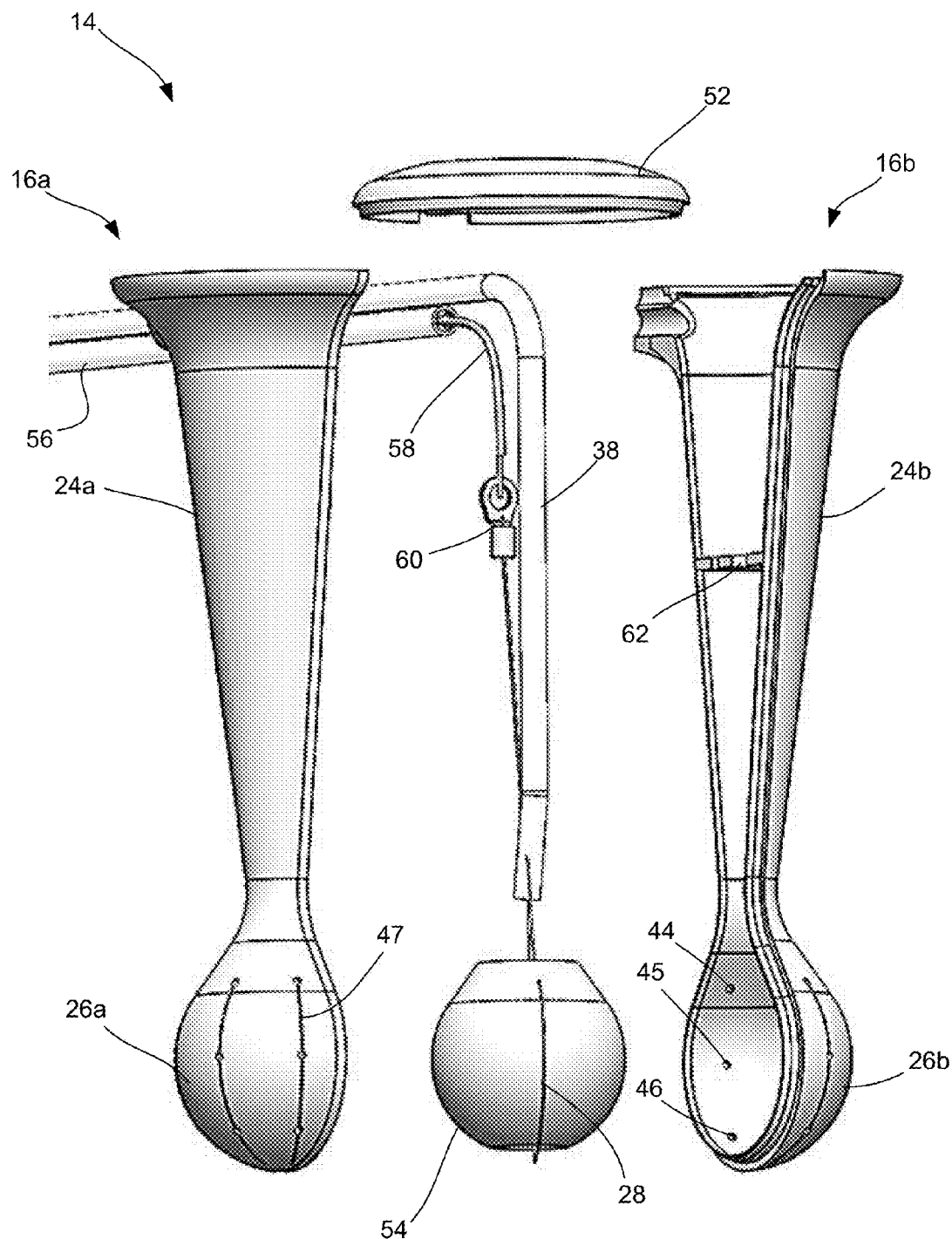
FIG. 8 is an exploded view of an ablation device consistent with the present disclosure, including a hydrophilic insert provided within an interior chamber of the distal portion and configured to receive a fluid from a fluid source and evenly distribute the fluid to an exterior an exterior surface of the distal portion, via weeping of the fluid through one or more perforations on the distal portion wall, to create a virtual electrode arrangement with the electrode array.

FIG. 8 is an exploded view of an ablation device 14 consistent with the present disclosure. As shown, in some implementations, the ablation device 14, specifically the distal tip 16, may be formed from two or more pieces (tip halves 16*a* and 16*b*) configured to be coupled to one another to form the unitary distal tip 16. Each half 16*a* and 16*b* includes cooperating neck portions 24*a*, 24*b* and spheroid bodies 26*a*, 26*b*, as well as a cap 52 to be coupled to both halves 16*a* and 16*b* so as to fully enclose the interior of the distal tip 16. As further illustrated, an electrical line 34 may be provided for coupling the conductive wires 28 to the controller 18 and ablation generator 20 and a fluid line 38 may be provided for providing a fluid connection between the irrigation pump or drip 22 to the distal tip 16 so as to provide a conductive fluid (e.g., saline) to the tip 16. The electrical line 34 and/or the fluid delivery line 38 can be supported by a stabilizing element 62 within the device lumen. In some cases, the stabilizing element 62 may be integral with the neck 24 of the distal tip 16.

As previously described, conductive members 28 extend through a first port (e.g., the distal port 44), run along an external surface of the spheroid body 26 (e.g. within the groove 47) before re-entering the lumen of the distal tip 16 through another port (e.g., the proximal port 46). A conductive fluid, such as saline, may be provided to the distal tip 16 via the fluid line 38, wherein the saline may be distributed through the ports (e.g., to the distal ports 44, the proximal ports 46, and/or medial ports 45). The saline weeping through the ports and to an outer surface of the distal tip 16 is able to carry electrical current from electrode array, such that energy is promoted from the electrode array to the tissue by way of the saline weeping from the ports, thereby creating a virtual electrode. Accordingly, upon the fluid weeping through the ports, a pool or thin film of fluid is formed on the exterior surface of the distal tip 16 and is configured to ablate surrounding tissue via the electrical current carried from the electrode array.

As shown, the ablation device 14 may further include hydrophilic insert 54 aligned with the fluid delivery line 38 and positioned within the interior chamber formed between the two halves 16*a*, 16*b*. The hydrophilic insert 40 is configured to distribute fluid (e.g., saline) delivered from the fluid line 38 through the distal tip 16 by, for example, wicking the saline against gravity. This wicking action improves the uniformity of saline distribution to the device ports (e.g., to the proximal ports 44, the distal ports 46, and/or a medial ports 45). The hydrophilic insert 40 can be formed from a hydrophilic foam material (e.g., hydrophilic polyurethane).

Figure 9:
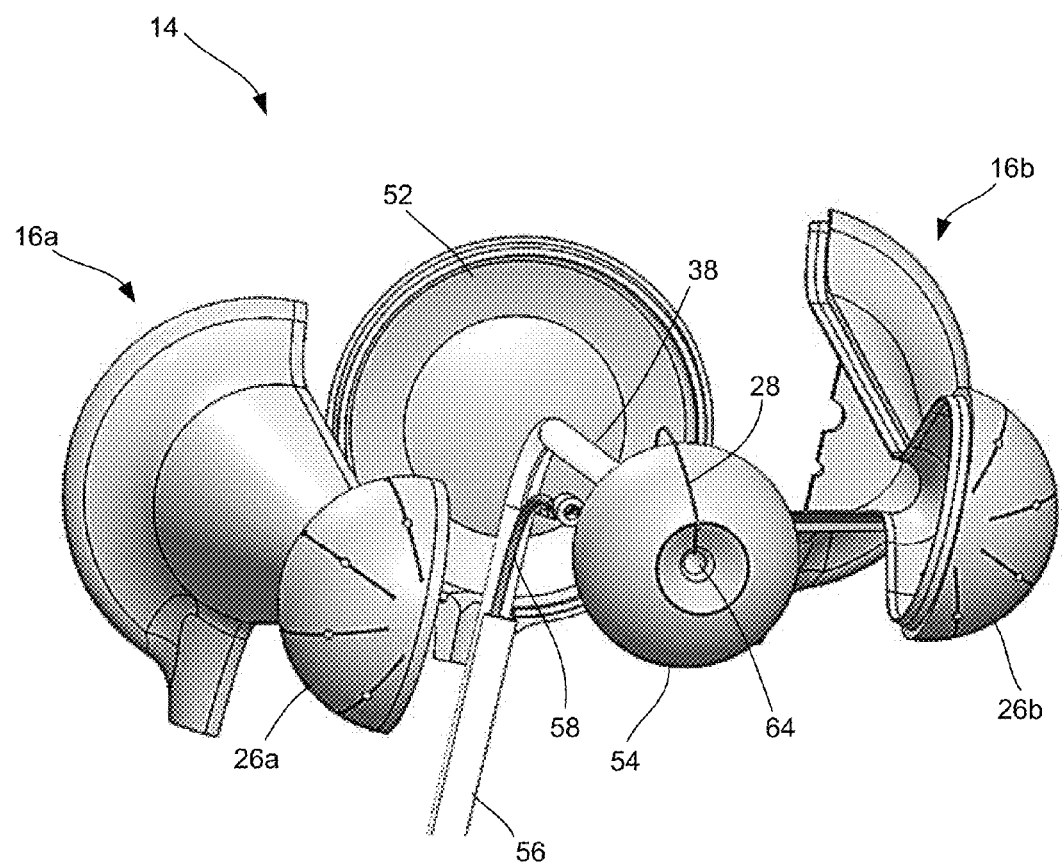
FIG. 9 is an exploded view of the ablation device of FIG. 8 illustrating the hydrophilic insert in more detail.
Figure 10:
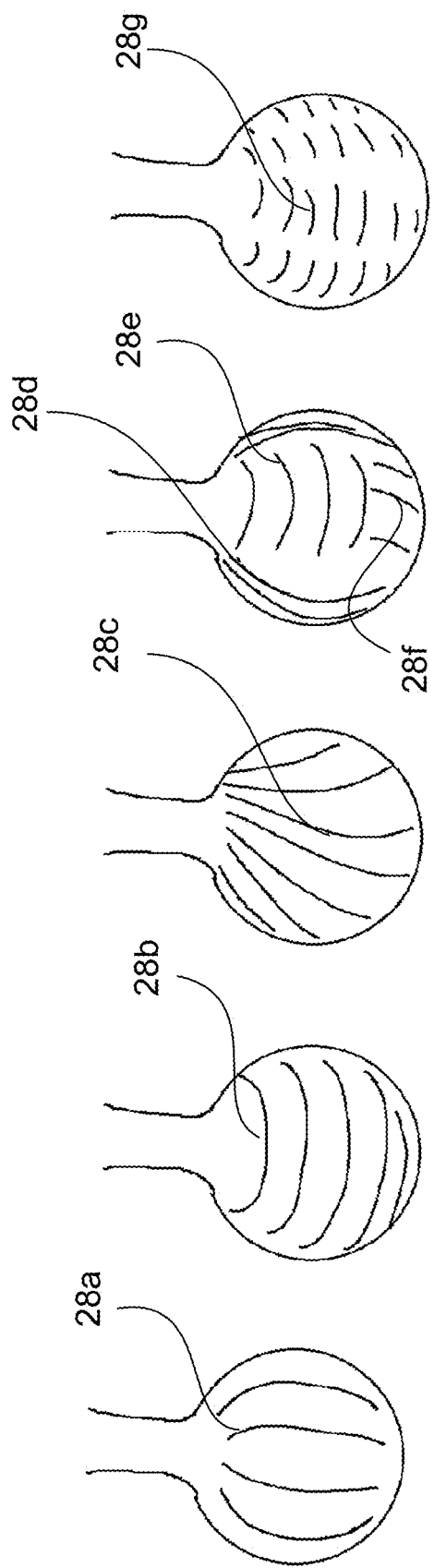
FIGS. 10A-10E are perspective views of a distal tip of the ablation device of FIG. 1 illustrating various electrode array configurations.

As shown in FIG. 9, for example, a conductive wire 28 passes within a lumen 64 of the hydrophilic insert 40 and along an external surface thereof. Similar to the conductive wires 28, the conductive wire 28 passing through the hydrophilic insert 54 is also electrically connected to the ablation generator 20. In some embodiments, the conductive member 28 is also configured to deploy the hydrophilic insert 40 from a delivery configuration to a deployed configuration (e.g., deployed as shown). For example, during use, the conductive member 28 can also contract or expand the hydrophilic insert 40 to modify the saline fluid flow as desired. For example, a control wire 58 may pass within the lumen of the tip 16, and may be grouped with other control wires (not shown) into a control line 56 that extends through the device lumen alongside the fluid delivery line 38. The control wires 58 can be connected to the conductive members 28 by a conductive link 60.

FIGS. 10A-10E are perspective views of a distal tip of the ablation device of FIG. 1 illustrating various electrode array configurations. In addition, while the conductive wires 28 have been described as extending along an external surface of the distal tip 16 in a direction that is parallel to the longitudinal axis of the device (as shown in a longitudinal configuration of conductive wires 28a in FIG. 10A), other configurations are possible. For example, one or more conductive wires 28b could extend along the external surface of the distal tip 16 in a direction that is perpendicular to the longitudinal axis of the device (as shown in a circumferential configuration in FIG. 10B). In other examples, one or more conductive wires 28c can extend from along the external surface of the distal tip 16 at an angle (e.g., non-parallel to the longitudinal axis of the device), as shown in an angled configuration in FIG. 10C. One or more conductive wires 28d, 28e, and 28f can also form a pattern along the external surface in which the conductive wires extend in various directions, as shown in a combined configuration in FIG. 10D. Additionally or alternatively, one or more conductive wires 28g can extend a reduced length of the external surface an alternative configuration in FIG. 10E.

While various conductive wires 28 have generally been described such that individual conductive members are energized or that the desired combination of conductive members is energized for a pre-selected or desired duration, in some cases, the desired combination of conductive members can be based on desired contact region of the distal tip 16.

Figure 11:
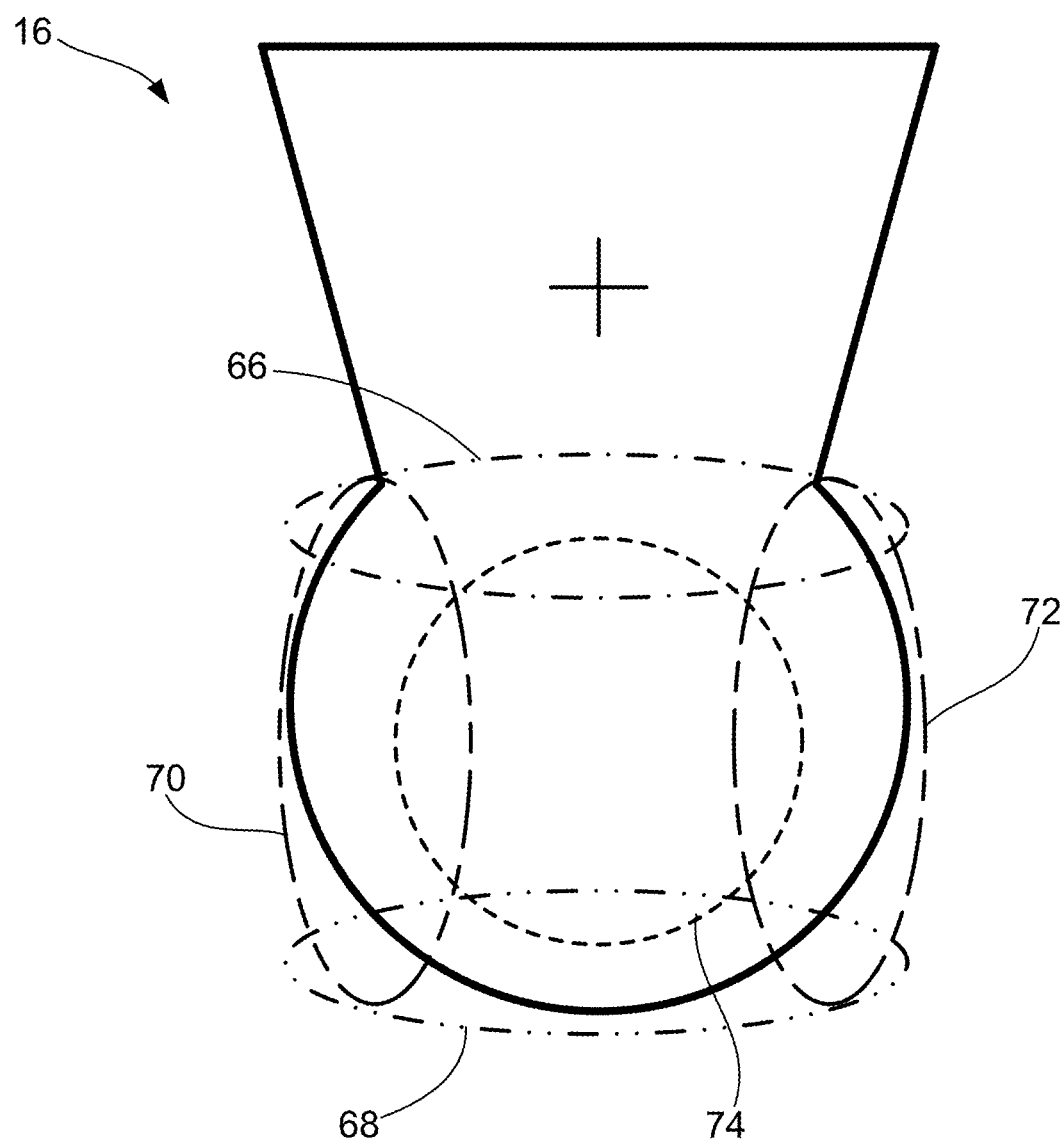
FIG. 11 is a side view of the distal tip of the ablation device of FIG. 1 including several clinical axes or sides. Each clinical axis or side includes one or more independently connected electrodes, which enables differential function and current independent drives and/or measurements.
Figure 12A:
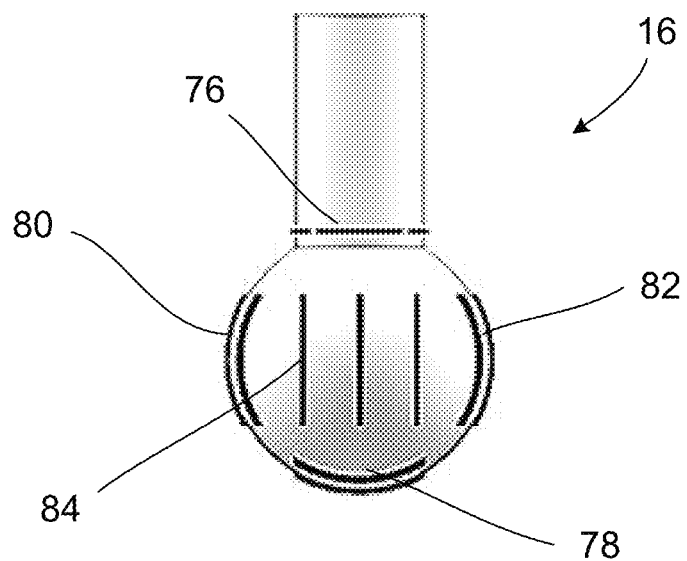
FIGS. 12A-12D are side and perspective views of the distal tip of the application device illustrating the different clinical axes or sides of FIG. 11.
Figure 12B:
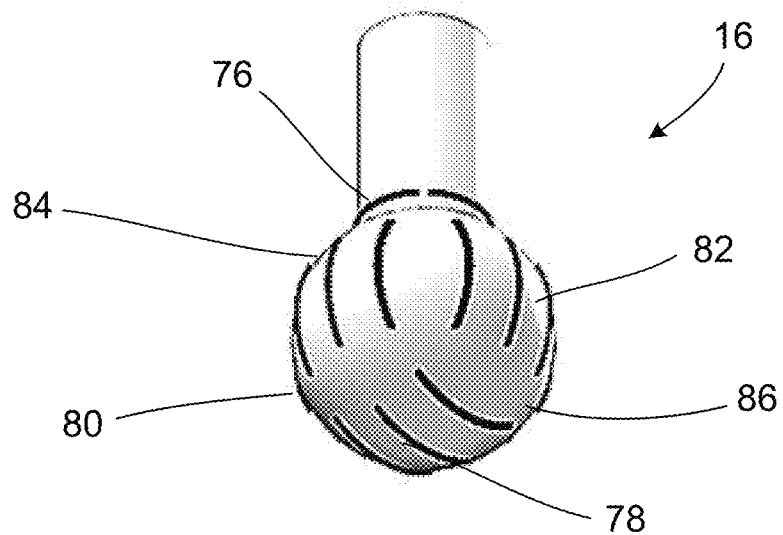
Figure 12C:
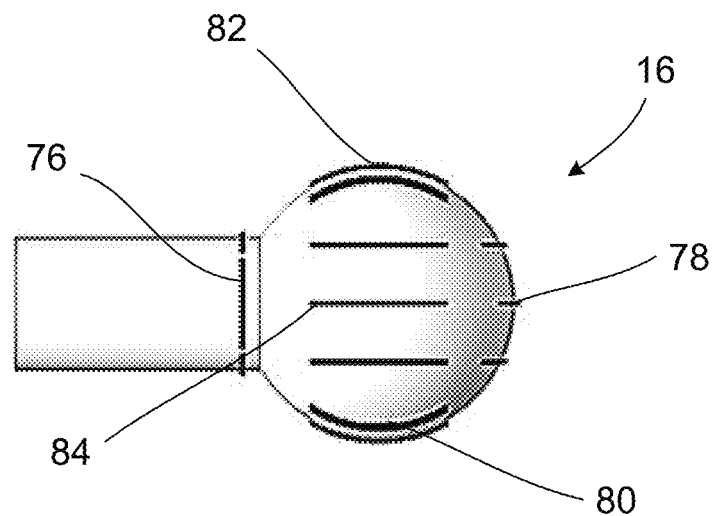
Figure 12D:
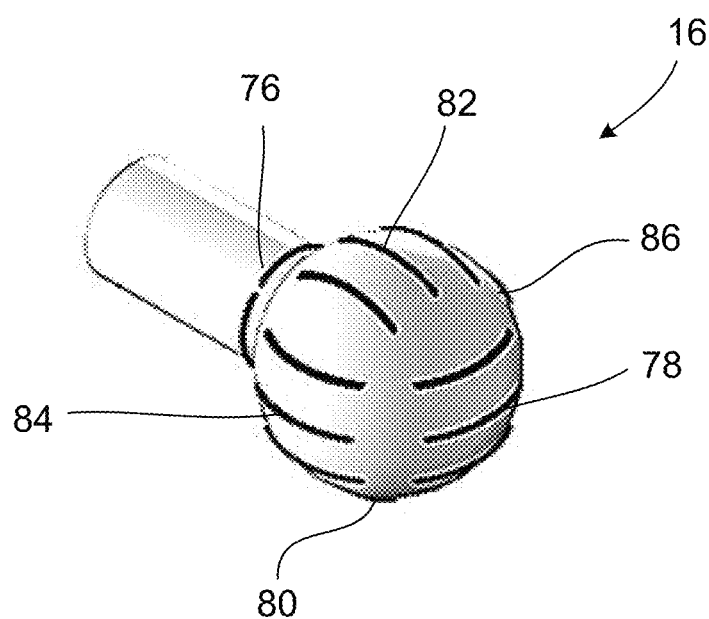

FIG. 11 is a side view of the distal tip 16 of the ablation device 14 of FIG. 1 including several clinical axes or sides. Each clinical axis or side includes one or more independently connected electrodes, which enables differential function and current independent drives and/or measurements. For example, referring to FIG. 11, the distal tip 16 can be divided into clinical axes or sides 66, 68, 70, 72, 74, and 75 (not shown). In other words, the distal tip 16 may include six clinical axes or sides of the distal portion (e.g, four sides or quadrants around spheroid body 70, 72, 74, and 75, and a top axis/side 66, and a bottom axis/side 68).

FIGS. 12A-12D are side and perspective views of the distal tip of the application device illustrating the different clinical axes or sides of FIG. 9. As shown in FIGS. 12A-12D, each clinical axis can include multiple independently connected conductive wires. For example, clinical axis/side 66 can include three independently connected conductive wires 76, clinical axis/side 68 can include three independently connected conductive wires 78, clinical axis/side 70 can include three independently controlled conductive wires 80, clinical axis/side 72 can include three independently connected conductive wires 82, clinical axis/side 74 can include three independently controlled conductive wires 84, and clinical axis/side 75 can include three independently controlled conductive wires 86. The independently connected conductive wires within each clinical axis or side allows for differential function and independent energy delivery and/or measurements. While FIGS. 12A-12D generally show three conductive wires for each clinical axis or side, other combinations are possible. For example, each of the clinical axes or sides can include a combination of conductive wires ranging from one conductive wire to ten or more conductive members.

FIGS. 13 and 14 are perspective and exploded perspective views, respectively, of one embodiment of a device controller 19 consistent with the present disclosure. As shown, the controller 19 may include a first halve or shell 88a and a second halve or shell 88b for housing a PC board 90 within, the PC board 90 comprising circuitry and hardware for controlling various parameters of the device 14 during an ablation procedure. The controller 19 further includes a display 92, such as an LCD or LED display for providing a visual representation of one or more parameters associated with the device 14, including, but not limited to, device status (e.g., power on/off, ablation on/off, fluid delivery on/off) as well as one or more parameters associated with the RF ablation (e.g., energy output, elapsed time, timer, temperature, conductivity, etc.). The controller 19 may further include a top membrane 94 affixed over the PC board 92 and configured to provide user input (by way of buttons or other controls) with which a user (e.g., surgeon or medical professional) may interact with a user interface provided on the display 92. The controller 19 may be configured to control at least the amount of electrical current applied to one or more of the conductive wires 28 from the ablation generator 20 and the amount of fluid to be delivered to the device 14 from the irrigation pump/drip 22.

Figure 15:
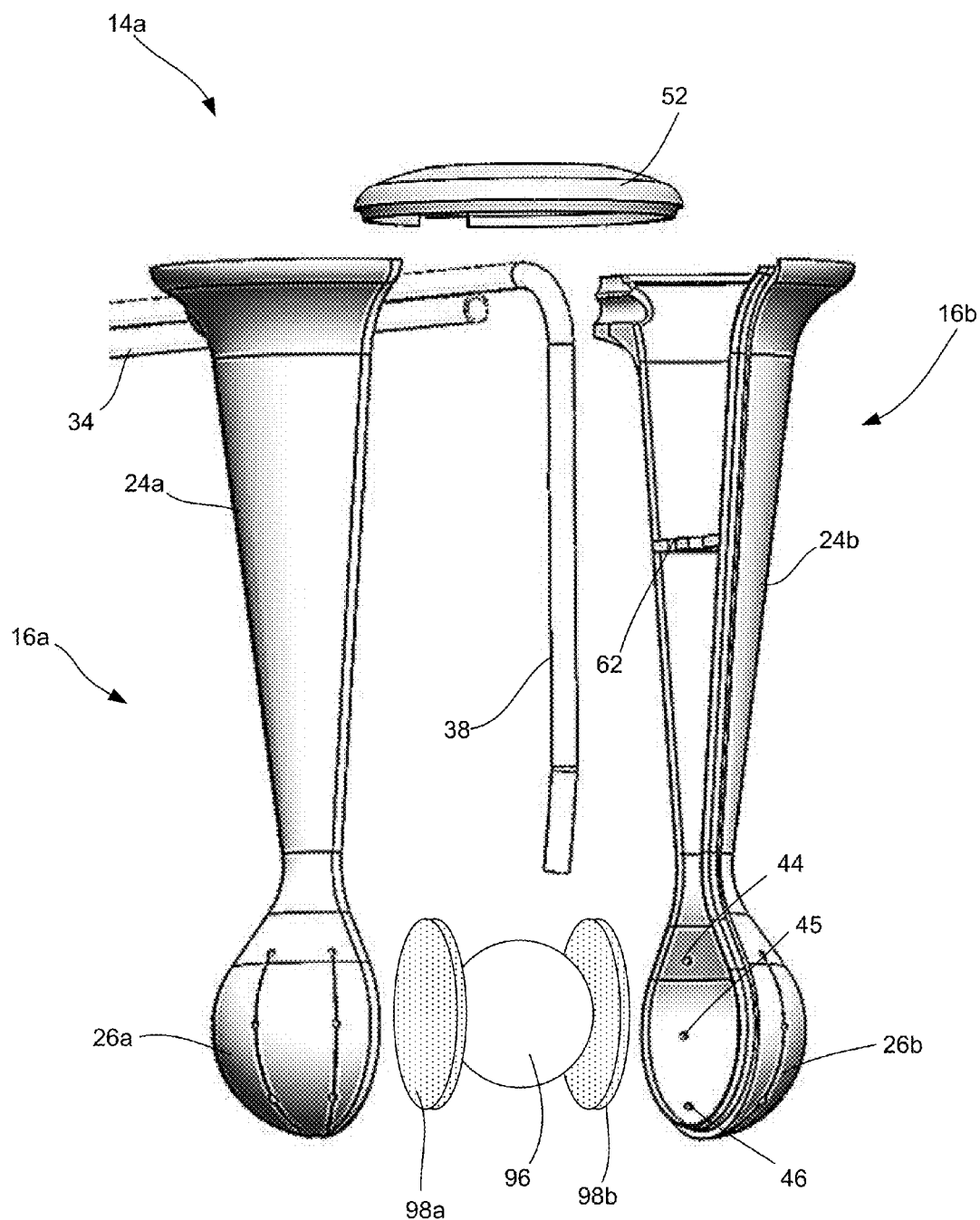
FIG. 15 is an exploded perspective view of another embodiment of an ablation device consistent with the present disclosure.

FIG. 15 is an exploded perspective view of another embodiment of an ablation device 14a consistent with the present disclosure. The device 14a is similarly configured as device 14 illustrated in FIG. 8, and includes similar elements. For example, the device 14a includes the distal tip 16 formed from two or more pieces (tip halves 16a and 16b) configured to be coupled to one another to form the unitary distal tip 16. Each half 16a and 16b includes cooperating neck portions 24a, 24b and spheroid bodies 26a, 26b, as well as a cap 52 to be coupled to both halves 16a and 16b so as to fully enclose the interior of the distal tip 16. As further illustrated, an electrical line 34 may be provided for coupling the conductive wires 28 to the controller 18 and ablation generator 20 and a fluid line 38 may be provided for providing a fluid connection between the irrigation pump or drip 22 to the distal tip 16 so as to provide a conductive fluid (e.g., saline) to the tip 16. The electrical line 34 and/or the fluid delivery line 38 can be supported by a stabilizing element 62 within the device lumen. In some cases, the stabilizing element 62 may be integral with the neck 24 of the distal tip 16.

The device 14a is configurd to provide RF ablation via a virtual electrode arrangement, which includes distribution of a fluid along an exterior surface of the distal tip 16 and, upon activation of the electrode array, the fluid may carry, or otherwise promote, energy emitted from the electrode array to the surrounding tissue. For example, the nonconductive spheroid body 26 includes an interior chamber (when the first and second halves 26a, 26b are coupled to one another) for retaining at least a spacing member 96 (also referred to herein as "spacer ball") and one or more hydrophilic inserts 98a, 98b surrounding the spacing member 96. The interior chamber of the distal tip 16 is configured to receive and retain a fluid (e.g., saline) therein from a fluid source. The hydrophilic inserts 98a, 98b are configured receive and evenly distribute the fluid through the distal tip 16 by wicking the saline against gravity. The hydrophilic inserts 98a and 98b can be formed from a hydrophilic foam material (e.g., hydrophilic polyurethane).

As previously described, the distal tip 16 may generally include a plurality of ports or apertures configured to allow the fluid to pass therethrough, or weep, from the interior chamber to an external surface of the distal tip 16. Accordingly, in some embodiments, all of the ports (e.g., proximal ports 44, medial ports 45, and distal ports 46) may be configured to allow for passage of fluid from the inserts 98a, 98b to the exterior surface of the distal tip 16. However, in some embodiments, only the medial ports 45 may allow for fluid passage, while the proximal and distal ports 44, 46 may be blocked via a heat shrink or other occlusive material.

The spacer member 96 may formed from a nonconductive material and may be shaped and sized so as to maintain the hydrophilic inserts 98a, 98b in sufficient contact with the interior surface of the distal tip wall, and specifically in contact with the one or more ports, such that the hydrophilic inserts 98a, 98b provides uniformity of saline distribution to the ports. In some embodiments, the spacer member 96 may have a generally spherical body, corresponding to the interior contour of the chamber of the spheroid body 26.

Accordingly, upon positioning the distal tip 16 within a target site (e.g., tissue cavity to be ablated), the electrode array can be activated and fluid delivery can be initiated. The fluid weeping through the ports to the exterior surface of the distal tip is able to carry energy from electrode array, thereby creating a virtual electrode. Accordingly, upon the fluid weeping through the port, a pool or thin film of fluid is formed on the exterior surface of the distal portion and is configured to ablate surrounding tissue via the RF energy carried from the electrode array.

Figure 16:
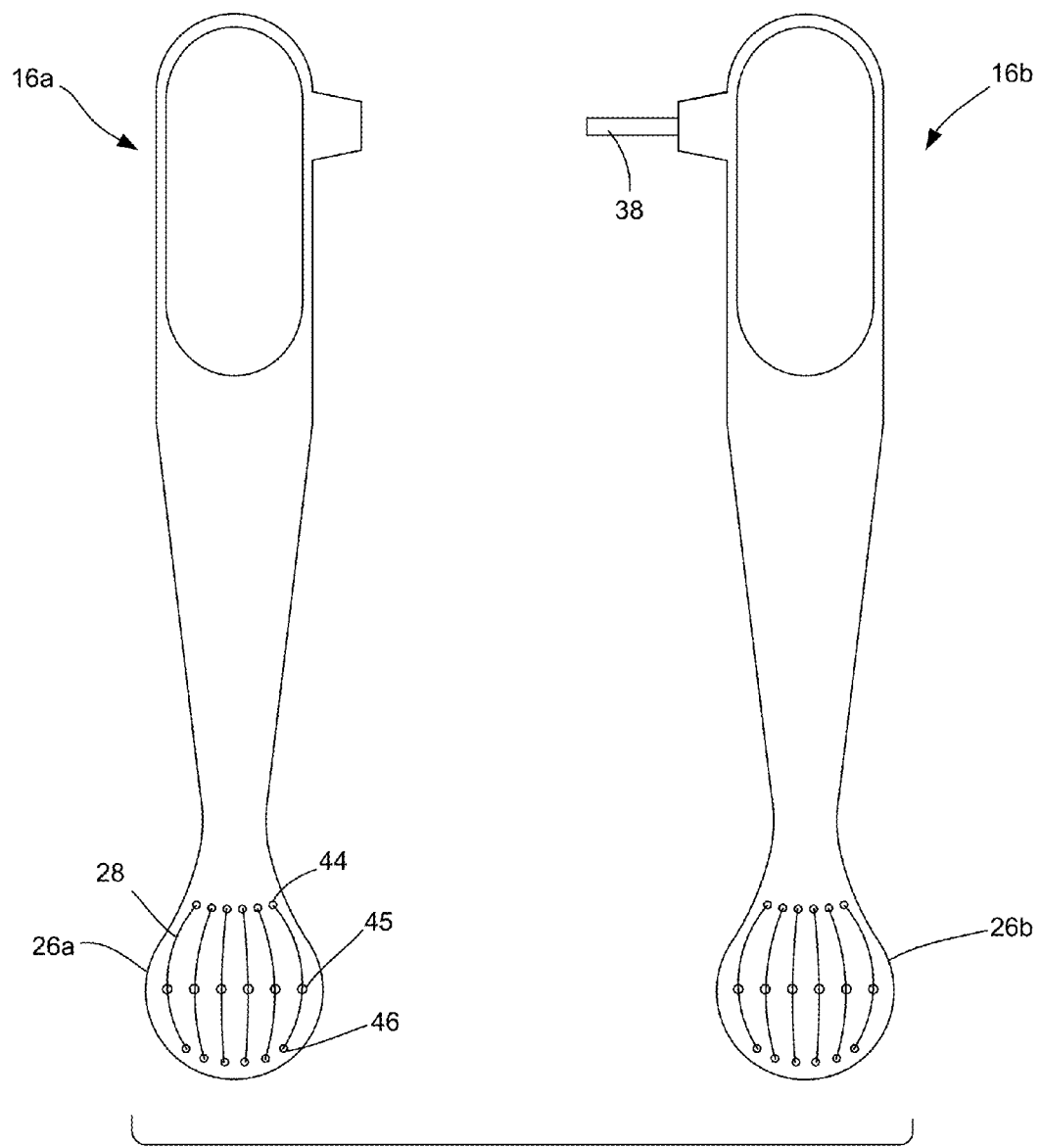
FIG. 16 is a plan view of the ablation device of FIG. 15 illustrating the two halves of the device separated from one another and showing the external surface of each.
Figure 17:
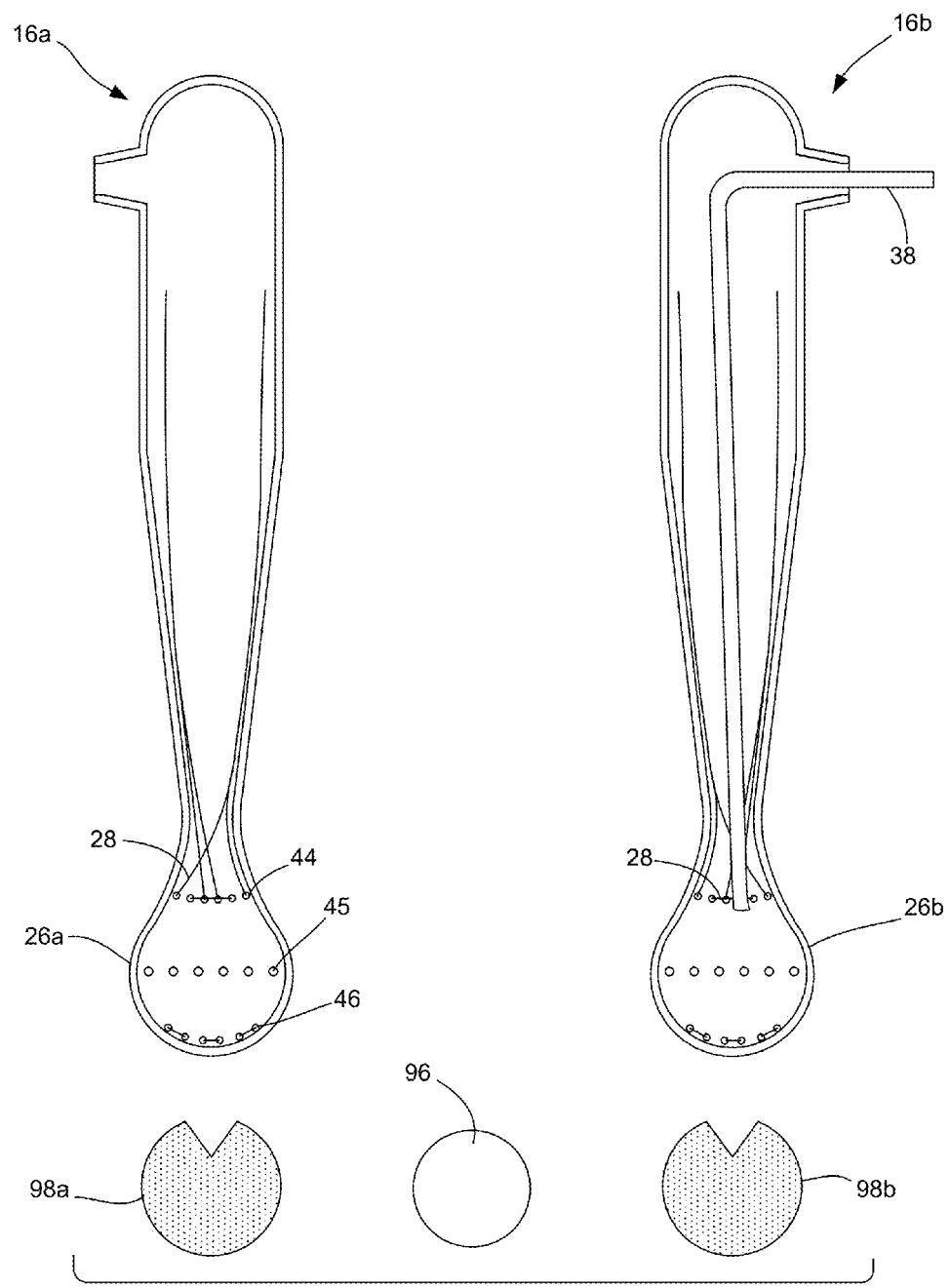
FIG. 17 is a plan view of the ablation device of FIG. 15 illustrating the two halves of the device separated from one another and showing the interior surface of each.

As previously described herein, conductive wires 28 may generally extend through a first port (e.g., the distal port 44), run along an external surface of the spheroid body 26 before re-entering the lumen of the distal tip 16 through another port (e.g., the proximal port 46). FIGS. 16, 17, 18A-18B, and 19A-19B illustrate another arrangement of conductive wires 28, in which at least four different conductive wires are provided, two of which serve as supply electrodes and the other two serve as return electrodes. Each of the four different conductive wires generally pass through at least two different proximal ports and two different distal ports, while remaining isolated from one another. FIG. 16 is a plan view of the ablation device 14a illustrating the two halves of the device tip 16a, 16b separated from one another and showing the external surface each, while FIG. 17 shows the interior surface of each.

Figure 18:
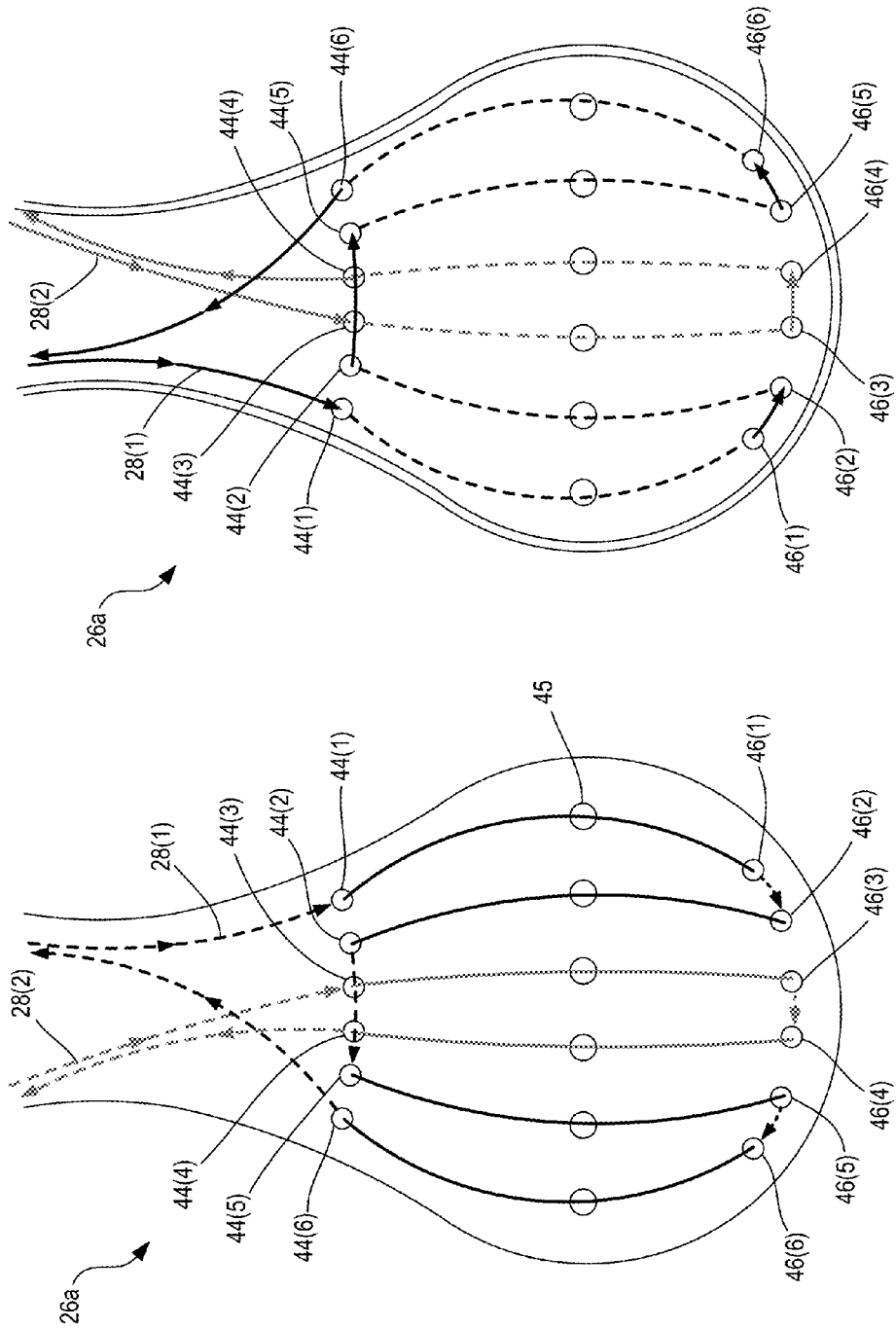
FIGS. 18A and 18B are enlarged views of the spheroid body of the first halve of the device showing the exterior and interior surfaces, respectively, and further illustrating the particular arrangement of first and second conductive wires extending through proximal and distal ports of the spheroid body.

FIGS. 18A and 18B are enlarged views of the spheroid body of the first halve 16a of the device 14a showing the exterior and interior surfaces, respectively, and further illustrating the particular arrangement of first and second conductive wires 28(1) and 28(2), partly in phantom, extending through proximal and distal ports 44, 46 of the spheroid body 26a. The following description of the first and second conductive wires 28(1) and 28(2) provides a general pathway of each wire, including passages through ports and extensions along lengths of the interior and exterior surfaces of the tip 16. In the illustrated embodiment, a first conductive wire 28(1) may serve as a return electrode while a second conductive wire 28(2) may serve as a supply electrode.

As shown, the first conductive wire 28(1) extends within the lumen of the tip 16a and passes through proximal port 44(1), extends along the exterior surface of the spheroid body 26a towards the distal ports (generally parallel to longitudinal axis of device), passes through distal port 46(1), extends along the interior surface of the body 26a towards adjacent distal ports (generally transverse to longitudinal axis of the device), passes through distal port 46(2), extends along the exterior surface of the spheroid body 26a back towards the proximal ports, passes through proximal port 44(2), extends along the interior surface of body 26a towards adjacent proximal ports, passes through proximal port 44(5), extends along the exterior surface of the spheroid body 26a back towards the distal ports, passes through distal port 46(5), extends along the interior surface of the body 26a towards adjacent distal ports, passes through distal port 46(6), extends along the exterior surface of the spheroid body 26a back towards the proximal ports, passes through proximal port 44(6), and extends back through lumen of the tip 16a. Accordingly, the first conductive wire 28(1) has at least four portions that extend along the exterior surface of the spheroid body 26a.

The second conductive wire 28(2) extends within the lumen of the tip 16a and passes through distal port 44(3), extends along the exterior surface of the spheroid body 26a towards the distal ports (generally parallel to longitudinal axis of device), passes through distal port 46(3), extends along the interior surface of the body 26a towards adjacent distal ports (generally transverse to longitudinal axis of the device), passes through distal port 46(4), extends along the exterior surface of the spheroid body 26a back towards the proximal ports, passes through proximal port 44(4), and extends back through lumen of the tip 16a. Accordingly, the second conductive wire 28(2) has at least two portions that extend along the exterior surface of the spheroid body 26a.

Figure 19:
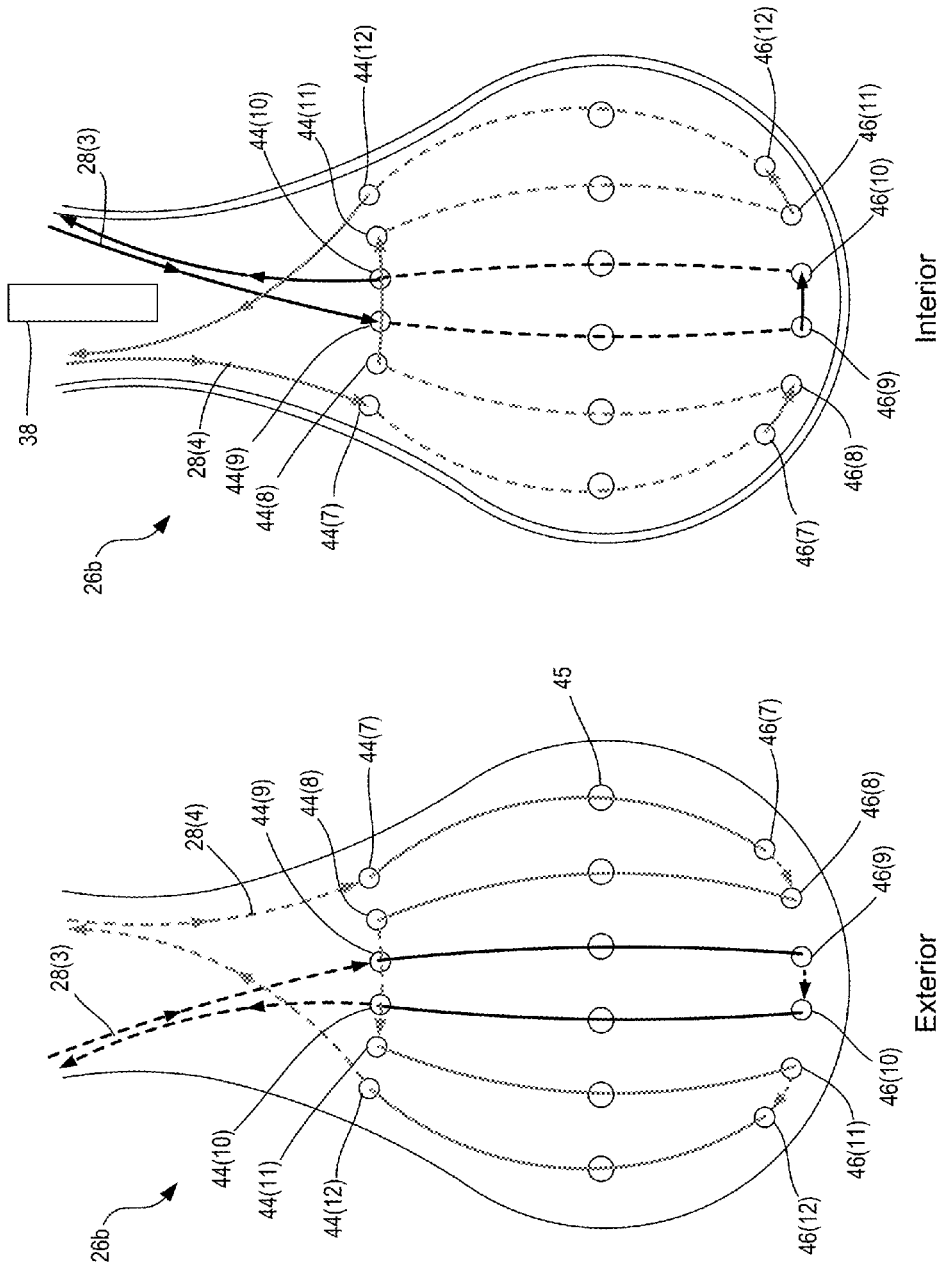
FIGS. 19A and 19B are enlarged views of the spheroid body of the second halve of the device showing the exterior and interior surfaces, respectively, and further illustrating the particular arrangement of third and fourth conductive wires extending through proximal and distal ports of the spheroid body.

FIGS. 19A and 18B are enlarged views of the spheroid body of the second halve 16b of the device 14a showing the exterior and interior surfaces, respectively, and further illustrating the particular arrangement of third and fourth conductive wires 28(3) and 28(4) extending through proximal and distal ports of the spheroid body 26b. The following description of the third and fourth conductive wires 28(3) and 28(4) provides a general pathway of each wire, including passages through ports and extensions along lengths of the interior and exterior surfaces of the tip 16. In the illustrated embodiment, a third conductive wire 28(3) may serve as a return electrode while a second conductive wire 28(4) may serve as a supply electrode.

As shown, the third conductive wire 28(3) extends within the lumen of the tip 16a and passes through proximal port 44(9), extends along the exterior surface of the spheroid body 26b towards the distal ports (generally parallel to longitudinal axis of device), passes through distal port 46(9), extends along the interior surface of the body 26b towards adjacent distal ports (generally transverse to longitudinal axis of the device), passes through distal port 46(10), extends along the exterior surface of the spheroid body 26b back towards the proximal ports, passes through proximal port 44(10), and extends back through lumen of the tip 16a. Accordingly, the third conductive wire 28(3) has at least two portions that extend along the exterior surface of the spheroid body 26b.

The fourth conductive wire 28(4) extends within the lumen of the tip 16b and passes through proximal port 44(7), extends along the exterior surface of the spheroid body 26*b* towards the distal ports (generally parallel to longitudinal axis of device), passes through distal port 46(7), extends along the interior surface of the body 26*b* towards adjacent distal ports (generally transverse to longitudinal axis of the device), passes through distal port 46(8), extends along the exterior surface of the spheroid body 26*b* back towards the proximal ports, passes through proximal port 44(8), extends along the interior surface of body 26*b* towards adjacent proximal ports, passes through proximal port 44(11), extends along the exterior surface of the spheroid body 26*b* back towards the distal ports, passes through distal port 46(11), extends along the interior surface of the body 26*b* towards adjacent distal ports, passes through distal port 46(12), extends along the exterior surface of the spheroid body 26*b* back towards the proximal ports, passes through proximal port 44(12), and extends back through lumen of the tip 16*a*.

Accordingly, the fourth conductive wire 28(4) has at least four portions that extend along the exterior surface of the spheroid body 26*b*.

Furthermore, each of the four conductive wires 28(1)-28(4) remain electrically isolated and independent from one another such that, each, or one or more sets of a combination of, the conductive wires, can independently receive an electrical current from the ablation generator and independently conduct energy, the energy including RF energy. This allows energy to be selectively delivered to a designated conductive wire or combination of conductive wires. This design also enables the ablation device to function in a bipolar mode because a first conductive wire (or combination of conductive wires) can deliver energy to the surrounding tissue through its electrical connection with an ablation generator while a second conductive wire (or combination of conductive wires) can function as a ground or neutral conductive member.

The independent control of each wire or sets of wires allows for activation (e.g., emission of RF energy) of corresponding portions of the electrode array. For example, the electrode array may be partitioned into specific portions which may correspond to clinical axes or sides of the distal portion of the device. In one embodiment, the electrode array may include at least four distinct portions (i.e., individual or sets of conductive wires) corresponding to four clinical axes or sides of the distal portion (e.g, four sides or quadrants around spheroid body).

Figure 20:
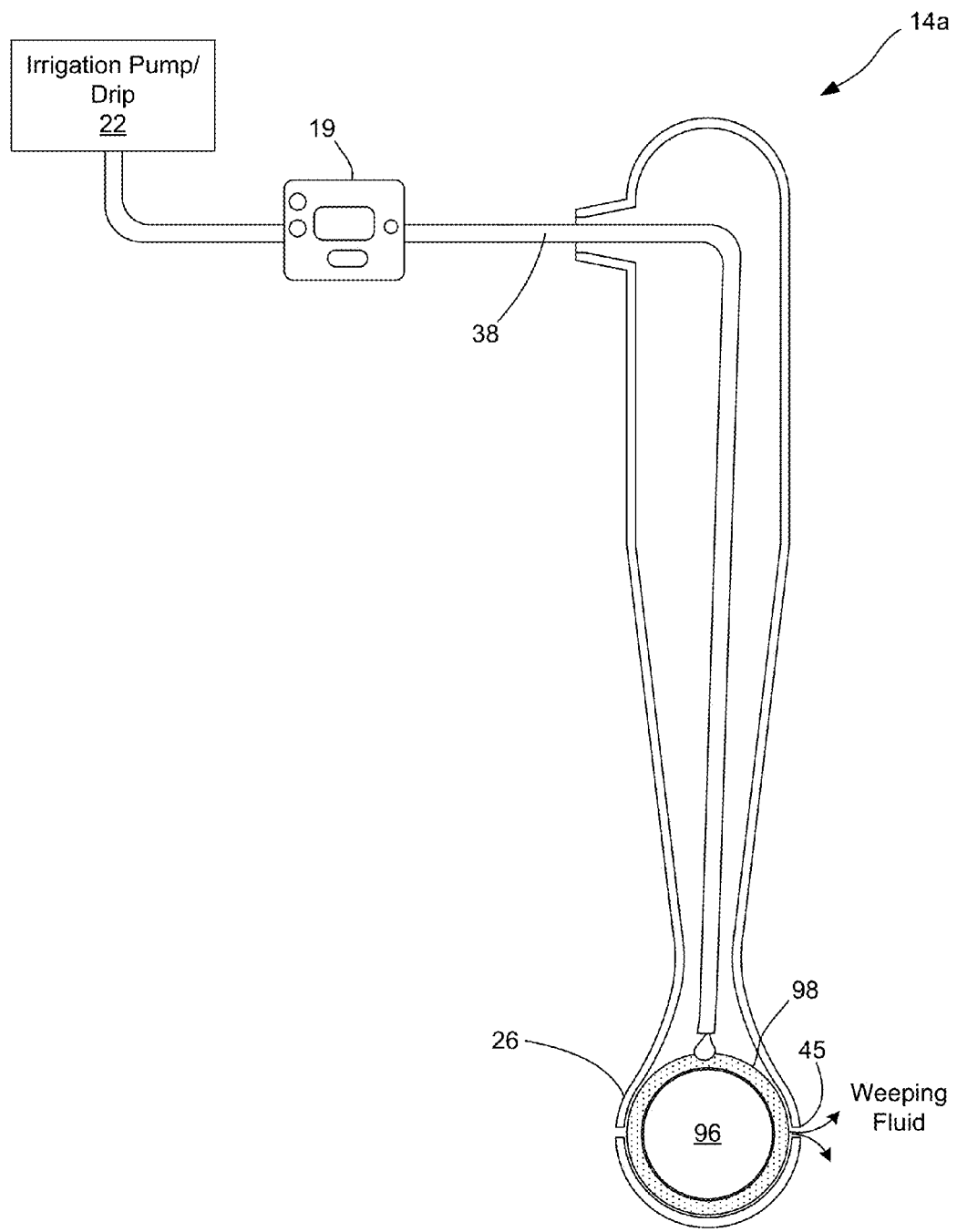
FIG. 20 is a schematic illustration of the ablation device of FIG. 15 illustrating delivery of fluid from the irrigation pump, as controlled by the controller, to the hydrophilic insert within the interior chamber of the distal portion of the device, wherein the fluid can be subsequently distributed to an exterior surface of the distal portion resulting in a virtual electrode arrangement upon activation of one or more portions of the electrode array.

FIG. 20 is a schematic illustration of the ablation device 14*a* illustrating delivery of fluid from the irrigation pump 22, as controlled by the controller 19, to the hydrophilic inserts 98*a*, 98*b* within the interior chamber of the distal tip 16, wherein the fluid can be subsequently distributed to an exterior surface of the spheroid body 26 resulting in a virtual electrode arrangement upon activation of one or more portions of the electrode array. As shown, the saline may be distributed through at least the medial ports 45, such that the weeping saline is able to carry electrical current from electrode array, such that energy is transmitted from the electrode array to the tissue by way of the saline weeping from the ports, thereby creating a virtual electrode. Accordingly, upon the fluid weeping through the medial port, a pool or thin film of fluid is formed on the exterior surface of the spheroid body 26 and is configured to ablate surrounding tissue via the electrical current carried from the electrode array.

Figure 21:
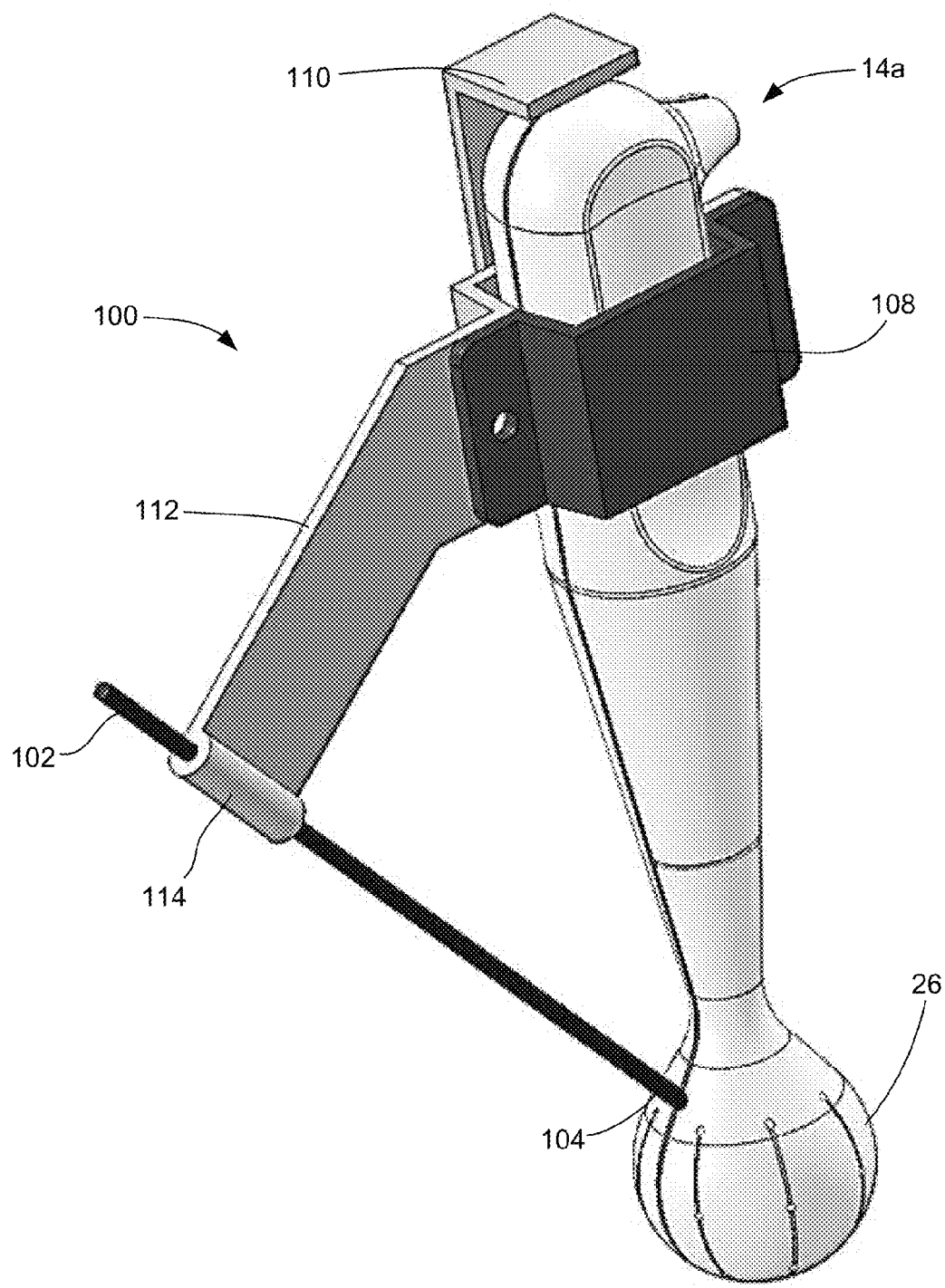
FIG. 21 is a perspective view of a detachable mount for holding a temperature probe (or any other separate monitoring device) at a desired position relative to the distal portion of the ablation device for the collection of temperature data during an RF ablation procedure.
Figure 22:
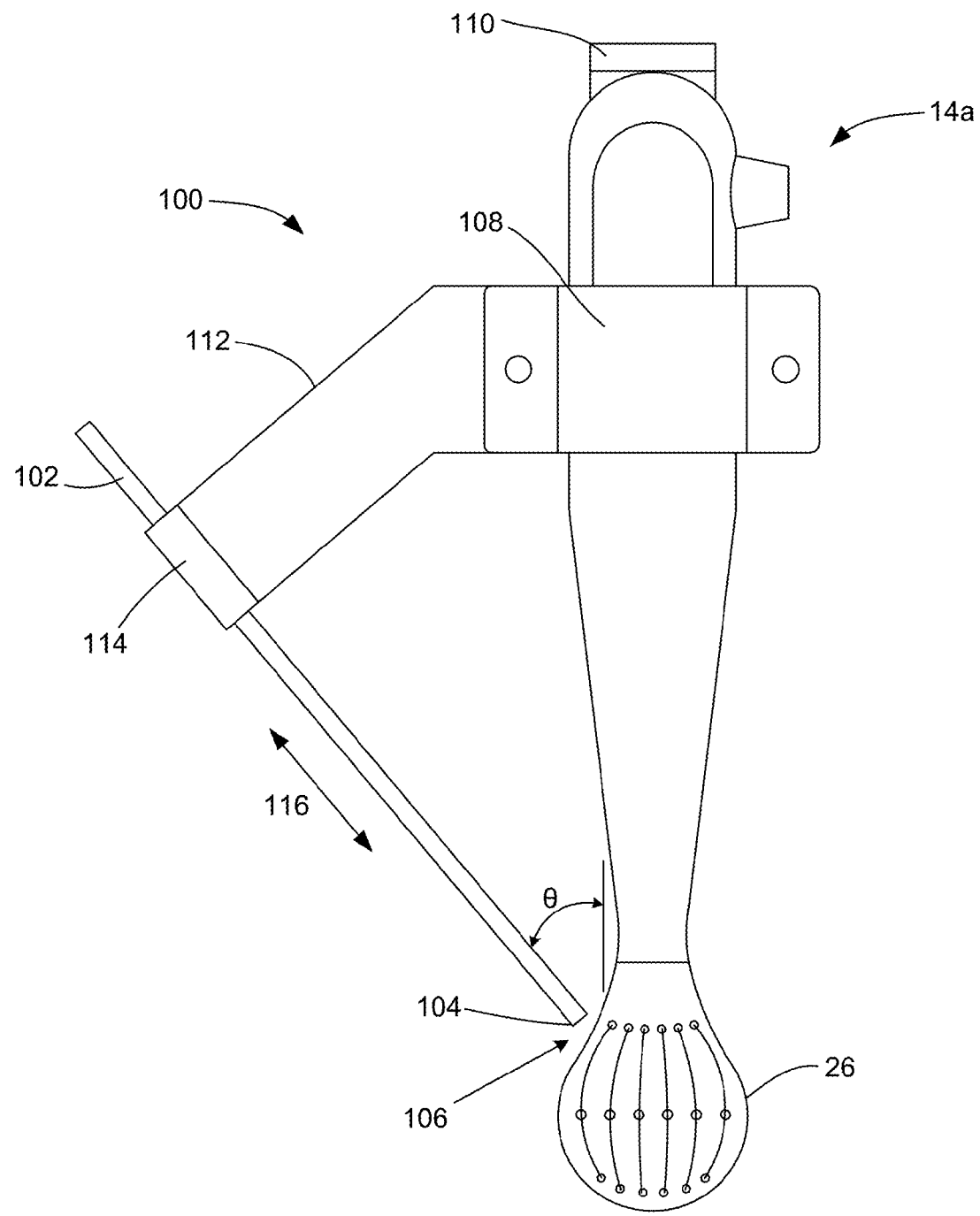
FIG. 22 is a plan view of the detachable mount holding the temperature probe relative to the distal portion of the ablation device.

FIGS. 21 and 22 are perspective and plan views of a detachable mount 100 for holding and maintaining a temperature probe 102 (or any other separate monitoring device) at a desired position, as indicated by arrow 106, relative to the spheroid body 26 of the distal tip of the ablation device 14. In particular, the mount 100 allows for an operator (e.g., surgeon) to releasably couple a temperature probe 102, or other measurement device, to the ablation device 14*a* and further position the working end 104 of the probe 102 in close proximity to the spheroid body 2 for the collection of temperature data during an RF ablation procedure.

As previously described herein, the controller 18, 19 may be configured to provide a surgeon with the ability to control ablation, such as controlling the supply of power to one or more conductive wires as well as control the delivery of fluid to the device tip 16. Furthermore, the controller 18, 19 may provide device status (e.g., power on/off, ablation on/off, fluid delivery on/off) as well as one or more parameters associated with the RF ablation (e.g., energy output, elapsed time, timer, temperature, conductivity, etc.). Thus, in some instances, it may be important to monitor at least the temperature adjacent to the device tip 16 during the ablation procedure, as well as pre-ablation and post-ablation, as temperature may be indicative of the status of surrounding tissue that is being, or is intended to be, ablated. Furthermore, it may be important to monitor the temperature at certain distances from the device tip 14 and at certain angles. Current devices may include a thermocouple mechanism integrated into the device. However, such configurations lack the ability to obtain temperature measurement at specific distances and angles relative to the ablation tip. The mount 100 is configured to provide a surgeon with the ability to adjacent the angle at which the temperature probe is positioned relative to the device tip 16 as well as the distance from the device tip 16, thereby overcoming the drawbacks of integrated thermocouples.

As shown, the mount 100 generally includes a body having a first end 108 configured to be releasably coupled to at least the proximal end of the device 14 by way of a clamping mechanism or latch-type engagement. The first end 108 includes a top guard member 110 configured to partially enclose at least the proximal end of the device 14, to further enhance securement of the mount 100 to the device 14. The mount 100 further includes an arm member 112 extending from the first end 108 and providing a second end 114 positioned a distance from the first end 108. The second end 114 is configured to hold the temperature probe 102 at a desired position, including a desired distance from the spheroid body 26 and a desired angle θ relative to the longitudinal axis of the ablation device. For example, in one embodiment, the second end 114 may include a bore or channel configured to receive and retain a portion of the temperature probe 102 within. The second end 114 may further allow for the temperature probe 102 to translate along the bore or channel, as indicated by arrow 116, to thereby adjust the distance of the temperature probe tip 104 relative to the spheroid body of the device tip. In some embodiments, the arm 112 and/or second end 114 may articulate relative to one another and/or the first end 108. Accordingly, the angle of the temperature probe 102 may also be adjusted as desired.

Accordingly, a tissue ablation devices, particularly the applicator heads described herein, may be well suited for treating hollow body cavities, such as cavities in breast tissue created by a lumpectomy procedure. The devices, systems, and methods of the present disclosure can help to ensure that all microscopic disease in the local environment has been treated. This is especially true in the treatment of tumors that have a tendency to recur.

As used in any embodiment herein, the term "controller", "module", "subsystem", or the like, may refer to software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices. "Circuitry", as used in any embodiment herein, may comprise, for example, singly or in any combination, hardwired circuitry, programmable circuitry such as computer processors comprising one or more individual instruction processing cores, state machine circuitry, and/or firmware that stores instructions executed by programmable circuitry. The controller or subsystem may, collectively or individually, be embodied as circuitry that forms part of a larger system, for example, an integrated circuit (IC), system on-chip (SoC), desktop computers, laptop computers, tablet computers, servers, smart phones, etc.

Any of the operations described herein may be implemented in a system that includes one or more storage mediums having stored thereon, individually or in combination, instructions that when executed by one or more processors perform the methods. Here, the processor may include, for example, a server CPU, a mobile device CPU, and/or other programmable circuitry.

Also, it is intended that operations described herein may be distributed across a plurality of physical devices, such as processing structures at more than one different physical location. The storage medium may include any type of tangible medium, for example, any type of disk including hard disks, floppy disks, optical disks, compact disk read-only memories (CD-ROMs), compact disk rewritables (CD-RWs), and magneto-optical disks, semiconductor devices such as read-only memories (ROMs), random access memories (RAMs) such as dynamic and static RAMs, erasable programmable read-only memories (EPROMs), electrically erasable programmable read-only memories (EEPROMs), flash memories, Solid State Disks (SSDs), magnetic or optical cards, or any type of media suitable for storing electronic instructions.

Other embodiments may be implemented as software modules executed by a programmable control device. The storage medium may be non-transitory.

As described herein, various embodiments may be implemented using hardware elements, software elements, or any combination thereof. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Reference throughout this specification to "one embodiment" or "an embodiment" means that a particular feature, structure, or characteristic described in connection with the embodiment is included in at least one embodiment. Thus, appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Accordingly, the claims are intended to cover all such equivalents.

What is claimed is:

1. A medical device for ablating tissue, the device comprising:
    a probe assembly comprising:
        a nonconductive handle including a lumen for receiving a conductive fluid from a fluid source;
        a nonconductive distal portion extending from the handle, the distal portion comprising a rigid spherical body of a fixed diameter defining an interior chamber in fluid communication with the lumen of the handle and configured to receive the conductive fluid therefrom, the rigid spherical body also defining a plurality of ports configured to allow passage of the conductive fluid from the interior chamber to an exterior surface of the rigid spherical body;
        a nonconductive spacing member disposed within the interior chamber; and
        a hydrophilic insert disposed within the interior chamber and surrounding the spacing member, the hydrophilic insert retained in place within the interior chamber between an exterior surface of the spacing member and an interior surface of the rigid spherical body, the hydrophilic insert configured to receive and evenly distribute the conductive fluid to the plurality of ports; and
    an electrode array comprising a plurality of independent conductive wires, each including a length positioned along the exterior surface of the rigid spherical body, wherein each of the plurality of wires, or one or more sets of a combination of wires, is configured to receive an electrical current and conduct energy to be carried by the conductive fluid passing through one or more of the plurality of ports for ablation of a target tissue.

2. The device of claim 1, wherein the plurality of ports comprises a plurality of proximal ports and distal ports, wherein each of the plurality of wires passes through at least one of the proximal ports and through a corresponding one of the distal ports, wherein each of the plurality of proximal ports corresponds to a separate one of the plurality of distal ports such that a portion of the conductive wire passing through a set of corresponding proximal and distal ports has a length that extends along the exterior surface of the distal portion between the corresponding proximal and distal ports.

3. The device of claim 2, wherein the wire extends along at least 20% of a length of the exterior surface of the distal portion.

4. The device of claim 2, wherein each of the plurality of conductive wires passes through a different distal port.

5. The device of claim 2, wherein each of the plurality of conductive wires passes through a different proximal port.

6. The device of claim 1, wherein the plurality of wires includes at least 2 wires, the wires are configured to axially translate along a longitudinal axis of the device.

7. The device of claim 1, wherein each of the plurality of wires is configured to conduct radiofrequency (RF) energy upon receipt of the electrical current.

8. The device of claim 1, wherein the electrode array comprises a plurality of different ablation portions arranged about the nonconductive distal portion of the handle.

9. The device of claim 8, wherein the plurality of different ablation portions comprises at least two clinical axes about the nonconductive distal portion of the handle.

10. The device of claim 9, wherein the at least two clinical axes comprise two quadrants of the electrode array.

11. The device of claim 8, wherein the each of the plurality of different ablation portions of the electrode array comprises at least one conductive wire.

12. The device of claim 1, wherein the plurality of ports comprises one or more medial ports on the nonconductive distal portion and configured to allow passage of the conductive fluid from the interior chamber to an exterior surface of the nonconductive distal portion.

\* \* \* \* \*